United States Patent
Maschino et al.

(10) Patent No.: US 7,706,874 B2
(45) Date of Patent: Apr. 27, 2010

(54) STIMULATING CRANIAL NERVE TO TREAT DISORDERS ASSOCIATED WITH THE THYROID GLAND

(75) Inventors: Steven E. Maschino, Seabrook, TX (US); Steven M. Parnis, Pearland, TX (US); William R. Buras, Friendswood, TX (US); Albert W. Guzman, League City, TX (US)

(73) Assignee: Cyberonics, Inc., Houston, TX (US)

( * ) Notice: Subject to any disclaimer, the term of this patent is extended or adjusted under 35 U.S.C. 154(b) by 1125 days.

(21) Appl. No.: 11/191,340

(22) Filed: Jul. 28, 2005

(65) Prior Publication Data
US 2007/0027483 A1  Feb. 1, 2007

(51) Int. Cl.
A61N 1/00  (2006.01)
(52) U.S. Cl. .................................................. 607/2
(58) Field of Classification Search .................. 607/2, 607/9, 48; 128/898
See application file for complete search history.

(56) References Cited

U.S. PATENT DOCUMENTS

| | | |
|---|---|---|
| 4,305,402 A | 12/1981 | Katims |
| 4,338,945 A | 7/1982 | Kosugi et al. |
| 4,431,000 A | 2/1984 | Butler et al. |
| 4,503,863 A | 3/1985 | Katims |
| 4,556,064 A | 12/1985 | Pomeranz et al. |
| 4,573,481 A | 3/1986 | Bullara |
| 4,590,946 A | 5/1986 | Loeb |
| 4,598,713 A | 7/1986 | Hansjurgens et al. |

(Continued)

FOREIGN PATENT DOCUMENTS

EP   1486232 A2   12/2004

(Continued)

OTHER PUBLICATIONS

Sjogren, M.D., Magnus et al.; Cognitive Effects of VNS Therapy in Patients with Alzheimer's Disease—Results of a One-Year Clinical Trial; 58th Annual Scientific Convention of the Society of Biological Psychiatry; May 15-17, 2003, San Francisco, CA.

(Continued)

Primary Examiner—George Manuel
(74) Attorney, Agent, or Firm—Williams, Morgan, & Amerson P.C.; Timothy L. Scott

(57) ABSTRACT

A method, system, and an apparatus for stimulating a cranial nerve of a patient to treat a disorder, such as a metabolic or an endocrine disorder associated with the thyroid gland with an implantable medical device are provided. The method comprises coupling an electrode to the cranial nerve selected from the group consisting of a vagus nerve, a trigeminal nerve, and a glossopharyngeal nerve. The method further includes generating an electrical signal to treat a disorder associated with the thyroid gland. The electrical signal may be applied to the cranial nerve using the electrode to provide electrical nerve stimulation therapy to the patient. For treating a patient with a metabolic or an endocrine disorder associated with the thyroid gland, a neurostimulator may be adapted to apply an electrical stimulus to the vagus nerve and/or a branch of the vagus nerve associated with the thyroid gland. By balancing hormonal imbalance, the neurostimulator may provide electrical nerve stimulation therapy to the patient, thereby treating a target metabolic or an endocrine disorder associated with the thyroid gland.

17 Claims, 10 Drawing Sheets

U.S. PATENT DOCUMENTS

| | | |
|---|---|---|
| 4,702,254 A | 10/1987 | Zabara |
| 4,793,353 A | 12/1988 | Borkan |
| 4,867,164 A | 9/1989 | Zabara |
| 5,025,807 A | 6/1991 | Zabara |
| 5,111,814 A * | 5/1992 | Goldfarb .................... 607/48 |
| 5,154,172 A | 10/1992 | Terry, Jr. et al. |
| 5,188,104 A | 2/1993 | Wernicke et al. |
| 5,199,428 A | 4/1993 | Obel et al. |
| 5,199,430 A | 4/1993 | Fang et al. |
| 5,215,086 A | 6/1993 | Terry, Jr. et al. |
| 5,231,988 A | 8/1993 | Wernicke et al. |
| 5,243,980 A | 9/1993 | Mehra |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,356,425 A | 10/1994 | Bardy et al. |
| 5,411,531 A | 5/1995 | Hill et al. |
| 5,423,872 A | 6/1995 | Cigaina |
| 5,514,175 A | 5/1996 | Kim et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,658,318 A | 8/1997 | Stroetmann et al. |
| 5,683,422 A | 11/1997 | Rise et al. |
| 5,690,681 A | 11/1997 | Geddes et al. |
| 5,690,691 A | 11/1997 | Chen et al. |
| 5,700,282 A | 12/1997 | Zabara |
| 5,702,428 A | 12/1997 | Tippey et al. |
| 5,707,400 A | 1/1998 | Terry, Jr. et al. |
| 5,755,750 A | 5/1998 | Petruska et al. |
| 5,766,231 A | 6/1998 | Erickson et al. |
| 5,792,186 A | 8/1998 | Rise |
| 5,792,210 A | 8/1998 | Wamubu et al. |
| 5,836,994 A | 11/1998 | Bourgeois |
| 5,861,014 A | 1/1999 | Familoni |
| 5,861,022 A | 1/1999 | Hipskind |
| 5,913,876 A | 6/1999 | Taylor et al. |
| 5,916,239 A | 6/1999 | Geddes et al. |
| 5,919,216 A | 7/1999 | Houben et al. |
| 5,995,872 A | 11/1999 | Bourgeois |
| 6,002,966 A | 12/1999 | Loeb et al. |
| 6,006,134 A | 12/1999 | Hill et al. |
| 6,026,326 A | 2/2000 | Bardy |
| 6,073,048 A | 6/2000 | Kieval et al. |
| 6,083,249 A | 7/2000 | Familoni |
| 6,091,992 A | 7/2000 | Bourgeois et al. |
| 6,097,984 A | 8/2000 | Douglas |
| 6,104,955 A | 8/2000 | Bourgeois |
| 6,104,956 A | 8/2000 | Naritoku et al. |
| 6,109,269 A | 8/2000 | Rise et al. |
| 6,115,635 A | 9/2000 | Bourgeois |
| 6,141,590 A | 10/2000 | Renirie et al. |
| 6,152,953 A | 11/2000 | Hipskind |
| 6,161,044 A | 12/2000 | Silverstone |
| 6,216,039 B1 | 4/2001 | Bourgeois |
| 6,233,488 B1 | 5/2001 | Hess |
| 6,240,316 B1 | 5/2001 | Richmond et al. |
| 6,259,951 B1 | 7/2001 | Kuzma et al. |
| 6,266,564 B1 | 7/2001 | Hill et al. |
| 6,304,787 B1 | 10/2001 | Kuzma et al. |
| 6,308,104 B1 | 10/2001 | Taylor et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,366,814 B1 | 4/2002 | Boveja et al. |
| 6,374,140 B1 | 4/2002 | Rise |
| 6,381,499 B1 | 4/2002 | Taylor et al. |
| 6,438,423 B1 | 8/2002 | Rezai et al. |
| 6,449,512 B1 | 9/2002 | Boveja |
| 6,473,644 B1 | 10/2002 | Terry, Jr. et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,542,776 B1 | 4/2003 | Gordon et al. |
| 6,556,868 B2 | 4/2003 | Naritoku et al. |
| 6,564,101 B1 | 5/2003 | Zikria |
| 6,564,102 B1 | 5/2003 | Boveja |
| 6,587,719 B1 | 7/2003 | Barrett et al. |
| 6,587,727 B2 | 7/2003 | Osorio et al. |
| 6,600,953 B2 | 7/2003 | Flesler et al. |
| 6,606,518 B1 | 8/2003 | Cigaina |
| 6,609,025 B2 * | 8/2003 | Barrett et al. .................. 607/2 |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,625,492 B2 | 9/2003 | Florio et al. |
| 6,628,987 B1 | 9/2003 | Hill et al. |
| 6,650,943 B1 | 11/2003 | Whitehurst et al. |
| 6,656,960 B2 | 12/2003 | Puskas |
| 6,668,191 B1 | 12/2003 | Boveja |
| 6,684,104 B2 | 1/2004 | Gordon et al. |
| 6,708,064 B2 | 3/2004 | Rezai |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,754,536 B2 | 6/2004 | Swoyer et al. |
| 6,775,573 B2 | 8/2004 | Schuler et al. |
| 6,788,970 B1 | 9/2004 | Park et al. |
| 6,788,975 B1 | 9/2004 | Whitehurst et al. |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,889,076 B2 | 5/2005 | Cigaina |
| 6,895,278 B1 | 5/2005 | Gordon |
| 6,907,295 B2 | 6/2005 | Gross et al. |
| 6,908,487 B2 | 6/2005 | Cigaina |
| 6,961,618 B2 | 11/2005 | Osorio et al. |
| 6,978,787 B1 * | 12/2005 | Broniatowski .............. 128/898 |
| 7,050,856 B2 | 5/2006 | Sypulkowski et al. |
| 2002/0099417 A1 | 7/2002 | Naritoku et al. |
| 2002/0116030 A1 | 8/2002 | Rezai |
| 2003/0236558 A1 | 12/2003 | Whitehurst et al. |
| 2004/0176812 A1 | 9/2004 | Knudson et al. |
| 2005/0010262 A1 | 1/2005 | Rezai et al. |
| 2005/0021092 A1 | 1/2005 | Yun et al. |
| 2005/0038484 A1 | 2/2005 | Knudson et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0177192 A1 | 8/2005 | Rezai et al. |
| 2005/0187590 A1 | 8/2005 | Boveja et al. |
| 2005/0192644 A1 | 9/2005 | Boveja et al. |
| 2005/0197675 A1 * | 9/2005 | David et al. .................. 607/9 |
| 2005/0283200 A1 | 12/2005 | Rezai |
| 2006/0009815 A1 | 1/2006 | Boveja |
| 2006/0079936 A1 | 4/2006 | Boveja |
| 2006/0085046 A1 | 4/2006 | Rezai et al. |

2006/0100667 A1   5/2006  Machado et al.

FOREIGN PATENT DOCUMENTS

| WO | 199302744 A1 | 2/1993 |
|---|---|---|
| WO | 20050-53788 A1 | 6/2005 |
| WO | 2005007120 A2 | 6/2005 |

OTHER PUBLICATIONS

Sheldon, M.D., PhD., Robert; Role of Pacing in the Treatment of Vasovagal Syncope; The American Journal of Cardiology, vol. 84 (8A); Oct. 21, 1999; pp. 26Q-32Q.

Satish R Raj, M.D. and Robert S. Sheldon, M.D., PhD.; Role of Pacemakers in Treating Neurocardiogenic Syncope; Cardiovascular Research Group, University of Calgary, Alberta, Canada, 2003; pp. 47-52.

Reese S. Terry, W. Brent Tarver and Jacob Zabara; The Implantable Neurocybernetic Prosthesis System; PACE, vol. 14, 1991; pp. 86-93.

Alejandro Valdez-Cruz et al.; Chronic Stimulation of the Cat Vagus Nerve Effect on Sleep and Behavior; Progress in Neuro-Psychopharmacology & Biological Psychiatry 26 (2002); pp. 113-118.

B.A. Malow, M.D., MS; et al.; Vagus Nerve Stimulation Reduces Daytime Sleepiness in Epilepsy Patients; Neurology 57; Sep. (1 of 2) 2001; pp. 879-884.

David Grundy and Tim Scratcherd; Sensory Afferents from the Gastrointestinal Tract; Handbook of Physiology—The Gastrointestinal System; Department of Physiology; University of Sheffield, UK; Chapter 16; pp. 593-619.

Stephen E. Epstein, M.D., et al.; The New England Journal of Medicine; "Treatment of Angina Pectoris by Electrical Stimulation of the Carotid-Sinus Nerves"; vol. 280, May 1, 1960; No. 18; pp. 971-978.

Christopher M. DeGiorgio, et al.; "Vagus Nerve Stimulation: Analysis of Device Parameters in 154 Patients During the Long-Term XE5 Study"; Epilepsia, vol. 42, No. 8, 2001; UCLA Department of Neurology; Revision Accepted Apr. 20, 2001; pp. 1017-1020.

Stuart J. Connolly, M.D., et al.; "Pacemaker Therapy for Prevention of Syncope in Patients with Recurrent Severe Vasovagal Syncope—Second Vasovagal Pacemaker Study (VPS II): A Randomized Trial"; JAMA, May 7, 2003; vol. 289, No. 17; pp. 2224-2229; downloaded from www.jama.com Dec. 5, 2006.

Kevin B. Clark, et al.; "Enhanced Recognition Memory Following Vagus Nerve Stimulation in Human Objects"; Nature Neuroscience, vol. 2, No. 1, Jan. 1, 1999; pp. 94-98.

K. B. Clark, et al.; "Posttraining Electrical Stimulation of Vagal Afferents with Concomitant Vagal Efferent Inactivation Enhances Memory Storage Processes in the Rat"; Neurology of Learning and Memory 70, pp. 364-373 (1998); Article No. NL983863.

Eugene Braunwald, M.D., et al.; "Relief of Angina Pectoris by Electrical Stimulation of the Carotid-Sinus Nerves"; The New England Journal of Medicine, Dec. 1967; vol. 227, No. 24; pp. 1278-1283.

Nina S. Braunwald, M.D., et al.; Carotid Sinus Nerve Stimulation for the Treatment of intractable Angine Pectoris: Surgical Technic; vol. 172; No. 5, Aug. 1969; pp. 870-876.

David S. Bachman, et al.; "Effects of Vagal Volleys and Serotonin on Units of Cingulate Cortex in Monkeys"; Laboratory of Brain Evolution and Behavior, National Institute of Mental Health, Bethesda, MD, 20014; Accepted Nov. 18, 1976; pp. 253-269.

Edited by: Sue Ritter, et al.; Department of Veterinary and Comparative Anatomy, Pharmacology and Physiology College of Veterinary Medicine, Washington State University, Pullman Washington: "Neuroanatomy and Physiology of Abdominal Vagal Afferents"; P.L. R. Andrews and I.N.C. Lawes: Chapter 12: A Protective Role for Vagal Afferents: An Hypothesis; pp. 281-302.

Reese S. Terry, W. Brent Tarver and Jacob Zabara; The Implantable Neurocybernetic Prosthesis System; PACE, vol. 14, 1991; pp. 86-93.

Sheldon, M.D., PhD., Robert; Role of Pacing in the Treatment of Vasovagal Syncope; The American Journal of Cardiology, vol. 84 (8A); Oct. 21, 1999; pp. 26Q-32Q.

Alejandro Valdez-Cruz et al.; Chronic Stimulation of the Cat Vagus Nerve Effect on Sleep and Behavior; Progress in Neuro-Psychopharmacology & Biological Psychiatry 26 (2002); pp. 113-118.

Edited by: Sue Ritter, et al.; Department of Veterinary and Comparative Anatomy, Pharmacology and Physiology College of Veterinary Medicine, Washington State University, Pullman Washintong: "Neuroanatomy and Physiology of Abdominal Vagal Afferents"; P.L. R. Andrews and I.N.C. Lawes: Chapter 12: A Protective Role for Vagal Afferents: An Hypopthesis; pp. 281-302.

* cited by examiner

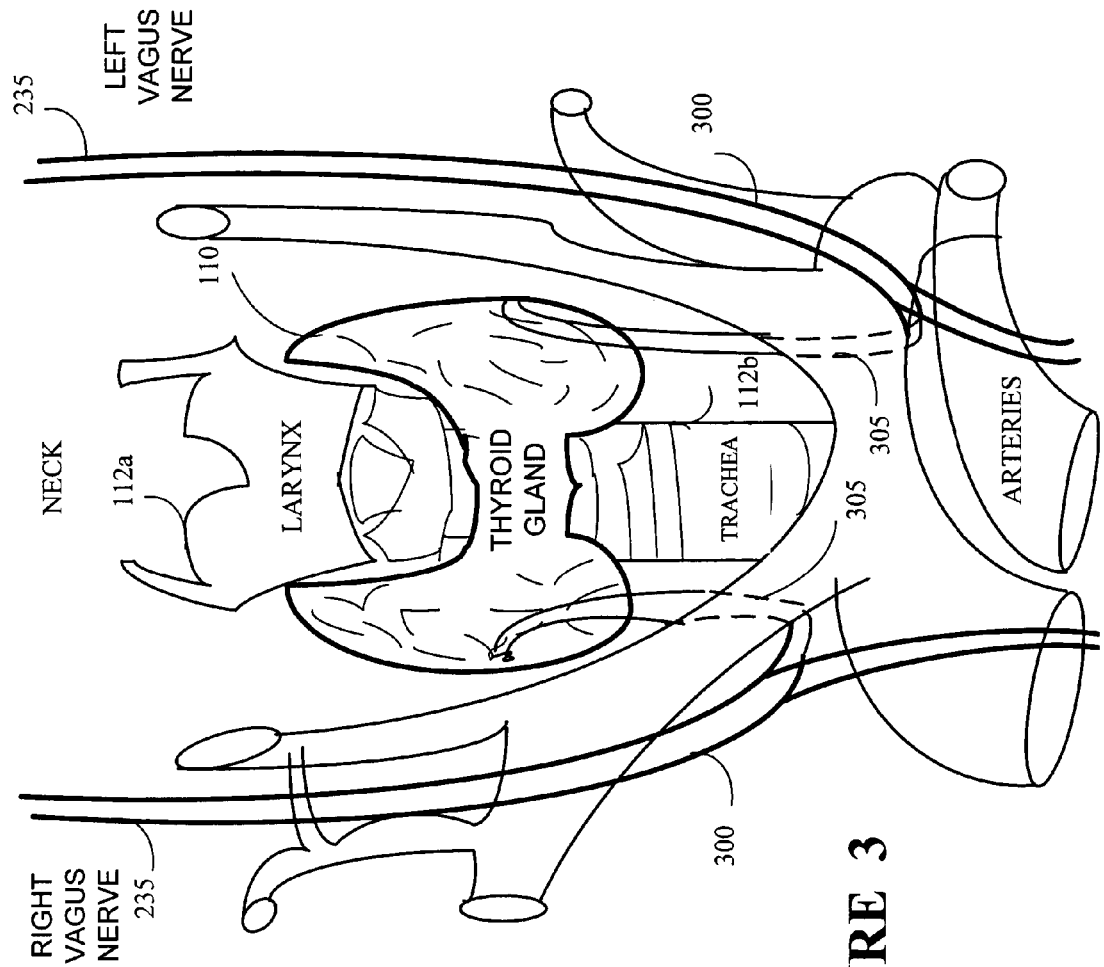

STIMULATING CRANIAL NERVE TO TREAT DISORDERS ASSOCIATED WITH THE THYROID GLAND

BACKGROUND OF THE INVENTION

1. Field of the Invention

This invention relates generally to implantable medical devices and, more particularly, to methods, apparatus, and systems for stimulating a cranial nerve of a patient to treat a medical condition, such as metabolic disorders and/or hormonal imbalance associated with the thyroid gland.

2. Description of the Related Art

The human nervous system (HNS) includes the brain and the spinal cord, collectively known as the central nervous system (CNS). The central nervous system comprises nerve fibers. The network of nerves in the remaining portions of the human body forms the peripheral nervous system (PNS). Some peripheral nerves, known as cranial nerves, connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions including blood pressure, body temperature, heartbeat and essentially all the unconscious activities that occur without voluntary control.

Like the rest of the human nervous system, nerve signals travel up and down the peripheral nerves, which link the brain to the rest of the human body. Nerve tracts or pathways, in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

The human body includes many endocrine glands such as the pituitary gland, the pancreas, the adrenal glands, the parathyroid gland, and the thyroid gland. The thyroid gland is located in the lower part of the neck and is shaped in a butterfly structure. The thyroid gland comprises two separate lobes that are inter-connected via thyroid tissue. The two lobes are located on the opposite sides of the windpipe called the trachea.

A number of cranial nerves innervate the vicinity of a person's larynx. For example, the thyroid gland is innervated by the vagus nerve (cranial nerve X). The trigeminal nerve (cranial nerve V), the glossopharyngeal nerve (cranial nerve IX), and the vagus nerve (cranial nerve X) provide branches to the pharyngeal plexus, which innervates muscles and mucosa of the pharynx and many of the muscles of the soft palate. The vagus nerve uses an innervating branch called inferior thyroid nerve originating from the recurrent laryngeal nerve. The recurrent laryngeal nerve is another branch of the vagus nerve, and it innervates the muscles of the larynx other than the cricothyroid.

Many chemical processes, such as metabolism process, transform food and oxygen into substances that any human body uses to perform various functions, such as operating different organs by stimulating different nerve fibers. Metabolism is generally responsible for cell activity that regulates body energy. However, the chemical balance in each body as well as the rate of metabolism differs from person-to-person. One known primary factor responsible for these two aspects of the human body is inheritance of certain genes. Other factors include lifestyle, cultural, eating, and emotional issues that may adversely affect the chemical balance and the rate of metabolism, resulting in one or more metabolic disorders.

Certain chemicals called hormones produced by human organs (e.g., the endocrine glands, such as the thyroid gland), may cause metabolic or hormonal disorders. Hormones work with the human nervous system to control various organs and tissues for ensuring a smooth, effective and normal functioning of disparate parts of the human body in a cooperative manner. Specifically, when a hormone is released into the bloodstream, only a target part(s) of the human body is affected. The thyroid gland provides the thyroxin hormone, which controls metabolism rates in the body. Another endocrine gland, the pituitary gland, produces a thyroid-stimulating hormone that is regulated by a thyroid-releasing hormone. The metabolism rate is based on the amount of the thyroxin hormone secreted by the thyroid gland.

The thyroid gland processes hormones that are essential to body metabolism. A malfunction of the thyroid gland may result in increased or decreased amounts of the thyroxin hormones, which may cause metabolic disorders. Examples of metabolic disorders include increased appetite, weight loss, increased sensitivity to heat, diarrhea, muscle wasting, sweating, tremors, heart palpitations, thyrotoxicosis, toxic goiter, Graves' disease, and shortness of breath. Besides a drug regimen or surgical intervention, effective treatments for such diseases and disorders are fairly limited. Additionally, patient may build resistance to the drug regimens and/or surgical intervention may be unadvisable in some situations.

SUMMARY OF THE INVENTION

In one aspect, the present invention comprises a method for stimulating a cranial nerve of a patient. The method includes coupling an electrode to the cranial nerve selected from the group consisting of a vagus nerve, a trigeminal nerve, and a glossopharyngeal nerve. The method further includes generating an electrical signal to treat a disorder associated with the thyroid gland and applying the electrical signal to the cranial nerve using the electrode.

In another aspect, a method of treating a patient having at least one of a metabolic and an endocrine disorder comprises coupling at least one electrode to at least one cranial nerve of the patient. The cranial nerve is selected from the group consisting of a vagus nerve, a trigeminal nerve, and a glossopharyngeal nerve. The method further includes providing a programmable electrical signal generator coupled to the electrode, generating an electrical signal with the electrical signal generator, applying the electrical signal to the electrode to treat the metabolic disorder, and detecting a symptom of the metabolic and/or the endocrine disorder, wherein the applying the electrical signal to the cranial nerve is initiated in response to the detecting the symptom.

In yet another aspect, the present invention comprises a method for stimulating a nerve branch associated with the thyroid gland. The method includes coupling at least one electrode to the nerve branch selected from the group consisting of a recurrent laryngeal nerve, an inferior thyroid nerve originating from the recurrent laryngeal nerve and an autonomic nerve of the autonomic nervous system. The method further includes generating an electrical signal to treat a disorder associated with the thyroid gland and applying the electrical signal to the nerve branch using the electrode.

In yet another aspect, the present invention comprises a method for stimulating a vagus nerve branch associated with the thyroid gland of a patient. The method includes coupling at least one electrode to the vagus nerve branch selected from the group consisting of a recurrent laryngeal nerve, an inferior thyroid nerve originating from the recurrent laryngeal nerve and an autonomic nerve of the autonomic nervous system. The method further includes generating an electrical signal to treat a disorder associated with the thyroid gland and applying the electrical signal to the vagus nerve branch using the electrode.

BRIEF DESCRIPTION OF THE DRAWINGS

The invention may be understood by reference to the following description taken in conjunction with the accompanying drawings, in which like reference numerals identify like elements, and in which:

FIG. 3 is a stylized schematic representation of a nerve structure including the vagus nerve associated with the thyroid gland to which the neurostimulator of the present invention may apply an afferent and/or an efferent neural signal, consistent with one exemplary embodiment of the present invention;

Figure 1:
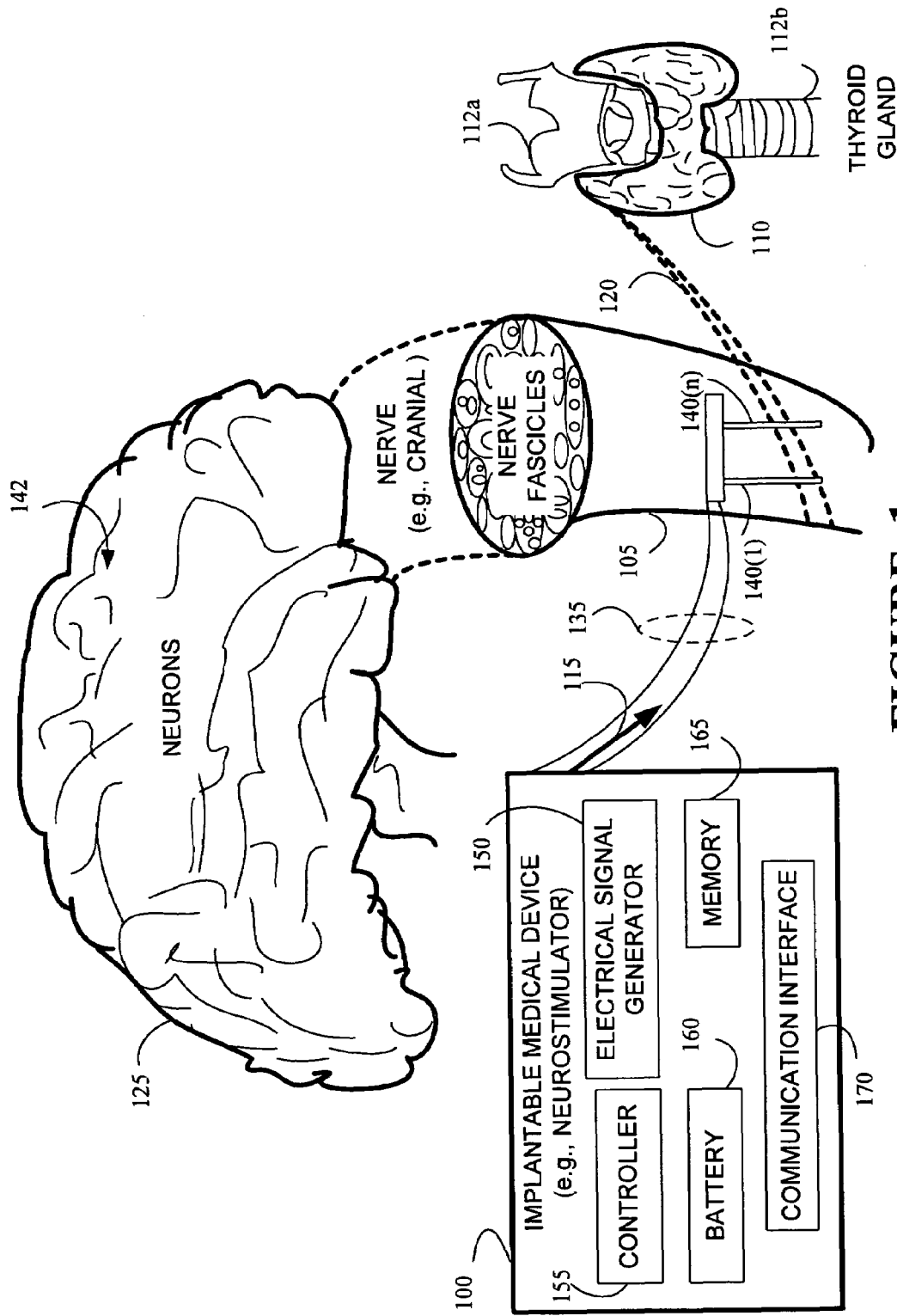
FIG. 1 is a stylized schematic representation of an implantable medical device that stimulates a cranial nerve for treating a patient with one or more disorders associated with the thyroid gland, such as metabolic and/or endocrine related hormonal imbalance according to one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

Embodiment of the present invention provide for the treatment of metabolic disorders by stimulation of nerves, such as cranial nerves.

Cranial nerve stimulation has been used successfully to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict. Accordingly, cranial nerve stimulation, and particularly vagus nerve stimulation, has not heretofore been deemed appropriate for use in treating vocal cord disorders.

In one embodiment of the present invention, methods, apparatus, and systems stimulate a cranial nerve, e.g., a vagus nerve, using an electrical signal to treat metabolic or hormonal disorders associated with an endocrine gland, such as the thyroid gland. "Electrical signal" on the nerve refers to the electrical activity (i.e., afferent and/or efferent action potentials) that are not generated by the patient's body and environment, rather applied from, an artificial source, e.g., an implanted neurostimulator. Disclosed herein is a method for treating disorders associated with the thyroid gland 110, such as metabolic or endocrine related hormonal imbalance associated with hormones of the thyroid gland using stimulation of the vagus nerve (cranial nerve X). One or more other cranial nerves may be stimulated in addition to the vagus nerve, including the trigeminal nerve (cranial nerve V), the vestibulocochlear nerve (cranial nerve VIII), and the glossopharyngeal nerve (cranial nerve IX), among others. Stimulation of the glossopharyngeal nerve may be used in treating hormonal disorders. A generally suitable form of neurostimulator for use in the method and apparatus of the present invention is disclosed, for example, in U.S. Pat. No. 5,154,172, assigned to the same assignee as the present application. The neurostimulator may be referred to as a NeuroCybernetic Prosthesis (NCP®, Cyberonics, Inc., Houston, Tex., the assignee of the present application). Certain parameters of the electrical stimuli generated by the neurostimulator are programmable, such as be means of an external programmer in a manner conventional for implantable electrical medical devices.

Turning now to FIG. 1, an implantable medical device (IMD) 100 is illustrated for stimulating a nerve, such as a cranial nerve 105 of a patient to treat disorders associated with the thyroid gland 110, such as metabolic or endocrine related hormonal imbalance using neurostimulation, according to one embodiment of the present invention. The term "cranial nerve" refers to any portion of the main trunk or any branch of the cranial nerve 105 including cranial nerve fibers, a left cranial nerve and a right cranial nerve. The thyroid gland 110 is located on the front of the neck under the larynx 112a and over the trachea 112b. The thyroid gland 110 produces a hormone called "thyroxin" that controls energy expenditure in the human body. The IMD 100 may deliver an electrical signal 115 to a nerve branch 120 of the cranial nerve 105 that travels to the brain 125 of a patient. The nerve branch 120 provides the electrical signal 115 to the thyroid gland 110. The nerve branch 120 may be a nerve branch of the cranial nerve 120 that is associated with the hormonal activity of the thyroid gland 110.

The IMD 100 may apply neurostimulation by delivering the electrical signal 115 to the nerve branch 120 via a lead 135 coupled to one or more electrodes 140 (1-n). For example, the IMD 100 may stimulate the cranial nerve 105 by applying the electrical signal 115 to the nerve branch 120 that directly couples to the thyroid gland 110 using the electrode(s) 140 (1-n). The cranial nerve 105 may be selected from the group consisting of a vagus nerve, a trigeminal nerve, and a glossopharyngeal nerve.

Consistent with one embodiment of the present invention, the IMD 100 may be a neurostimulator device capable of treating a disease, disorder or condition associated with the hormonal activity of the thyroid gland 110 by providing electrical neurostimulation therapy to a patient. To this end, the IMD 100 may be implanted in the patient at a suitable location. The implanted medical device 100 may apply the electrical signal 115, which may comprise an electrical pulse signal, to the cranial nerve 105. The IMD 100 may generate the electrical signal 115 based on an amount of thyroid hormone or a thyroid-stimulating hormone in the blood and/or detect a thyroid-stimulating biochemical function of the patient relative to a value within a predetermined range.

The IMD 100 may apply the electrical signal 115 to the nerve branch 120 or a nerve fascicle within the cranial nerve 105. By applying the electrical signal 115, the IMD 100 may treat or control disorders associated with the thyroid gland 110, such as metabolic or endocrine related to hormonal imbalance in a patient.

Implantable medical devices 100 that may be used in the present invention include any of a variety of electrical stimulation devices, such as a neurostimulator capable of stimulating a neural structure in a patient, especially for stimulating a patient's cranial nerve such as a vagus nerve. The IMD 100 is capable of delivering a controlled current stimulation signal. Although the IMD 100 is described in terms of cranial nerve stimulation, and particularly vagus nerve stimulation (VNS), a person of ordinary skill in the art would recognize that the present invention is not so limited. For example, the IMD 100 may be applied to the stimulation of other cranial nerves, such as the trigeminal and/or glossopharyngeal nerves, or other neural tissue, such as one or more brain structures of the patient.

In the generally accepted clinical labeling of cranial nerves, the tenth cranial nerve is the vagus nerve, which originates from the stem of the brain 125. The vagus nerve passes through foramina of the skull to parts of the head, neck and trunk. The vagus nerve branches into left and right branches, or vagi, upon exiting the skull. Left and right vagus nerve branches include both sensory and motor nerve fibers. The cell bodies of vagal sensory nerve fibers are attached to neurons located outside the brain 125 in ganglia groups, and the cell bodies of vagal motor nerve fibers are attached to neurons 142 located within the gray matter of the brain 125. The vagus nerve is a parasympathetic nerve, part of the peripheral nervous system (PNS). Somatic nerve fibers of the cranial nerves are involved in conscious activities and connect the CNS to the skin and skeletal muscles. Autonomic nerve fibers of these nerves are involved in unconscious activities and connect the CNS to the visceral organs such as the heart, lungs, stomach, liver, pancreas, spleen, and intestines. Accordingly, to provide vagus nerve stimulation (VNS), a patient's vagus nerve may be stimulated unilaterally or bilaterally in which a stimulating electrical signal is applied to one or both the branches of the vagus nerve, respectively.

For example, coupling the electrodes 140(1-n) comprises coupling an electrode to at least one cranial nerve selected from the group consisting of the left vagus nerve and the right vagus nerve. The term coupling may include actual fixation, proximate location, and the like. The electrodes 140(1-n) may be coupled to a branch of the vagus nerve of the patient. The nerve branch 120 may be selected from the group consisting of a recurrent laryngeal nerve, an inferior thyroid nerve originating from the recurrent laryngeal nerve and an autonomic nerve of the autonomic nervous system (ANS). The thyroid gland 110 receives innervations from sympathetic and parasympathetic nerve fibers of the autonomic nervous system. The sympathetic fibers arise from the cervical ganglia and enter with blood vessels, whereas the parasympathetic fibers are derived from the vagus nerve and reach the thyroid gland via branches of the laryngeal nerves. The recurrent laryngeal nerves and the parathyroid glands are located on the posterior surface of the lateral lobes of the thyroid gland 110. The recurrent laryngeal nerves reside in a cleft between the trachea 112b and the esophagus.

A number of cranial nerves innervate the vicinity of the larynx 112a. The trigeminal nerve (cranial nerve V), glossopharyngeal nerve (cranial nerve IX), and the vagus nerve (cranial nerve X) provide branches to the pharyngeal plexus, which innervates muscles and mucosa of the pharynx and many of the muscles of the soft palate. The superior laryngeal nerve is a branch of the vagus nerve, which itself branches to an external branch and an internal branch. The external branch of the superior laryngeal nerve innervates the sternohyoid, the cricothyroid, and part of the constrictor pharynges inferior muscle. The internal branch of the superior laryngeal nerve innervates the glands of the epiglottis, the base of the tongue, the aryepiglottic fold, and the larynx superior to the vocal folds. The recurrent laryngeal nerve is another branch of the vagus nerve, and it innervates the muscles of the larynx other than the cricothyroid.

Applying the electrical signal 115 to a selected cranial nerve 105 may comprise generating a response selected from the group consisting of an afferent action potential, an efferent action potential, an afferent hyperpolarization, a sub-threshold depolarization and an efferent hyperpolarization. The IMD 100 may generate an afferent action potential for treating disorders associated with the thyroid gland 110, such as metabolic or endocrine related hormonal imbalance of the patient. For example, if a patient has a hypothyroid condition, the IMD 100 may treat the patient by restoring a euthyroid state. A patient with Graves' disease or other thyrotoxic states may be treated for restoring a euthyroid state and to prevent thyroid storm, a severe hyperthyroidism. Thyroid storm generally results in tachycardia, or cardiac arrhythmias, fever, disorientation, coma, and even death. The IMD 100 may apply the electrical signal 115 to the nerves to the vocal cords (recurrent laryngeal nerves) of a patient to treat a temporary or a permanent loss of function of the vocal cord based on disorders associated with the thyroid gland 110, such as metabolic or endocrine related hormonal imbalance.

IMD 100 may comprise an electrical signal generator 150 and a controller 155 operatively coupled thereto to generate the electrical signal 115 for causing the nerve stimulation. The stimulus generator 150 may generate the electrical signal 115. The controller 155 may be adapted to apply the electrical signal 115 to the cranial nerve 105 to provide electrical neurostimulation therapy to the patient for treating a metabolic disorder associated with the thyroid gland 110. The controller 155 may direct the stimulus generator 150 to generate the electrical signal 115 to stimulate the vagus nerve.

To generate the electrical signal 115, the IMD 100 may further include a battery 160, a memory 165 and a communication interface 170. More specifically, the battery 160 may comprise a power-source battery that may be rechargeable. The battery 160 provides power for the operation of the IMD 100, including electronic operations and the stimulation function. The battery 160, in one embodiment, may be a lithium/thionyl chloride cell or, in another embodiment, a lithium/carbon monofluoride cell. The memory 165, in one embodiment, is capable of storing various data, such as operation parameter data, status data, and the like, as well as program code. The communication interface 170 is capable of providing transmission and reception of electronic signals to and from an external unit. The external unit may be a device that is capable of programming the IMD 100.

The IMD 100, which may be a single device or a pair of devices, is implanted and electrically coupled to the lead(s) 135, which are in turn coupled to the electrode(s) 140 implanted on the left and/or right branches of the vagus nerve, for example. In one embodiment, the electrode(s) 140 (1-n) may include a set of stimulating electrode(s) separate from a set of sensing electrode(s). In another embodiment, the same electrode may be deployed to stimulate and to sense. A particular type or a combination of electrodes may be selected as desired for a given application. For example, an electrode suitable for coupling to a vagus nerve may be used. The electrodes 140 may comprise a bipolar stimulating electrode pair. Those skilled in the art having the benefit of the present invention will appreciate that many electrode designs could be used in the present invention.

Using the electrode(s) 140(1-n), the stimulus generator 150 may apply a predetermined sequence of electrical pulses to the selected cranial nerve 105 to provide therapeutic neurostimulation for the patient with a metabolic disease or a hormonal disorder. While the selected cranial nerve 105 may be the vagus nerve, the electrode(s) 140(1-n) may comprise at least one nerve electrode for implantation on the patient's vagus nerve for direct stimulation thereof. Alternatively, a nerve electrode may be implanted on a branch of the patient's vagus nerve for direct stimulation thereof.

A particular embodiment of the IMD 100 may be a programmable electrical signal generator. Such a programmable electrical signal generator may be capable of programmably defining the electrical signal 115. By using at least one parameter selected from the group consisting of a current magnitude, a pulse frequency, and a pulse width, the IMD 100 may treat a metabolic disorder. The IMD 100 may detect a symptom of the metabolic disorder. In response to detecting the symptom, the IMD 100 may initiate applying the electrical signal 115. For example, a metabolic imbalance sensor may be used to detect the symptom. To treat the metabolic disorder, the IMD 100 may apply the electrical signal 115 during a first treatment period and further apply a second electrical signal to the cranial nerve 105 using the electrode 140 during a second treatment period.

In one embodiment, the method may further include detecting a symptom of the metabolic disorder, wherein the applying the electrical signal 115 to the cranial nerve 105 is initiated in response to the detecting of the symptom. In a further embodiment, the detecting the symptom may be performed by the patient. This may involve a subjective observation that the patient is experiencing a symptom of the metabolic disorder. Alternatively, or in addition, the symptom may be detected by performing a metabolic disorder test on the patient. Further still, a symptom may be detected by visualizing body function by an EKG, MRI, or PET scan to observe any metabolic imbalance response typical of metabolic disorder.

The method may be performed under a single treatment regimen or under multiple treatment regimens. "Treatment regimen" herein may refer to a parameter of the electrical signal 115, a duration for applying the signal, and/or a duty cycle of the signal, among others. In one embodiment, the applying the electrical signal 115 to the cranial nerve 105 is performed during a first treatment period, and may further include the step of applying a second electrical signal to the cranial nerve using the electrode 146 during a second treatment period. In a further embodiment, the method may include detecting a symptom of the metabolic disorder, wherein the second treatment period is initiated upon the detection of the symptom. For example, a patient suffering a metabolic disorder typically presents a set of chronic symptoms. However, another patient who also periodically suffers acute episodes of the metabolic disorder presents a set of symptoms that is different from or more intense than one or more chronic symptoms. This patient may benefit by receiving a first electrical signal during a first, chronic treatment period and a second electrical signal during a second, acute treatment period. Three or more treatment periods may be used, if deemed desirable by a medical practitioner.

Figure 2:
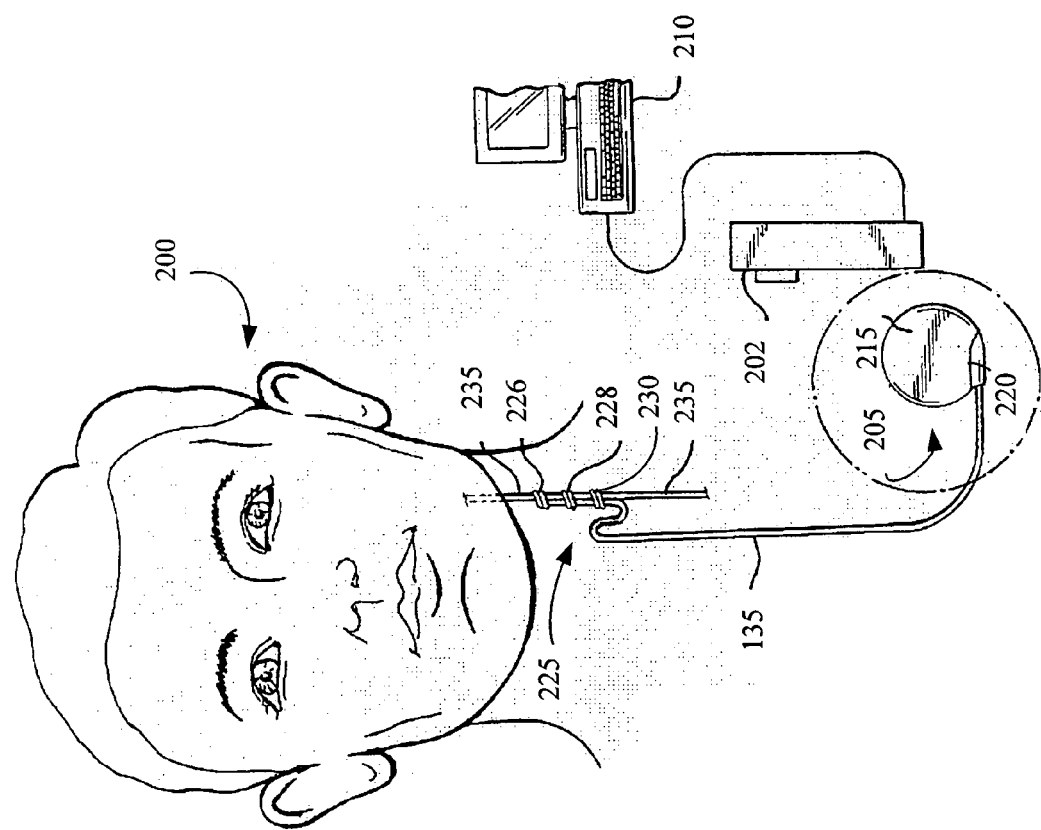
FIG. 2 illustrates one embodiment of a neurostimulator implanted into a patient's body for stimulating the vagus nerve of the patient, with an external programming user interface, in accordance with an illustrative embodiment of the present invention.

A particular embodiment of the IMD 100 shown in FIG. 1 is illustrated in FIG. 2. As shown therein, an electrode assembly 225, which may comprise a plurality of electrodes such as electrodes 226, 228, may be coupled to the cranial nerve 105 such as vagus nerve 235 in accordance with an illustrative embodiment of the present invention. The lead 135 is coupled to the electrode assembly 225 and secured, while retaining the ability to flex with movement of the chest and neck. The lead 135 may be secured by a suture connection to nearby tissue. The electrode assembly 225 may deliver the electrical signal 115 to the cranial nerve 105 to cause desired nerve stimulation for treating a metabolic disorder. Using the electrode(s) 226, 228, the selected cranial nerve such as vagus nerve 235, may be stimulated within a patient's body 200.

Although FIG. 2 illustrates a system for stimulating the left vagus nerve 235 in the neck (cervical) area, those skilled in the art having the benefit of the present disclosure will understand the electrical signal 105 for nerve stimulation may be applied to the right cervical vagus nerve in addition to, or instead of, the left vagus nerve, and remain within the scope of the present invention. In one such embodiment, lead 135 and electrode 225 assemblies substantially as discussed above may be coupled to the same or a different electrical signal generator.

An external programming user interface 202 may be used by a health professional for a particular patient to either initially program and/or to later reprogram the IMD 100, such as a neurostimulator 205. The neurostimulator 205 may include the electrical signal generator 150, which may be programmable. To enable physician-programming of the electrical and timing parameters of a sequence of electrical impulses, an external programming system 210 may include a processor-based computing device, such as a computer, personal digital assistant (PDA) device, or other suitable computing device.

Using the external programming user interface 202, a user of the external programming system 210 may program the neurostimulator 205. Communications between the neurostimulator 205 and the external programming system 210 may be accomplished using any of a variety of conventional techniques known in the art. The neurostimulator 205 may include a transceiver (such as a coil) that permits signals to be communicated wirelessly between the external programming user interface 202, such as a wand, and the neurostimulator 205.

The neurostimulator 205 having a case 215 with an electrically conducting connector on header 220 may be implanted in the patient's chest in a pocket or cavity formed by the implanting surgeon just below the skin, much as a pacemaker pulse generator would be implanted, for example. A stimulating nerve electrode assembly 225, preferably comprising an electrode pair, is conductively connected to the distal end of an insulated electrically conductive lead assembly 135, which preferably comprises a pair of lead wires and is attached at its proximal end to the connector on the case 215. The electrode assembly 225 is surgically coupled to a vagus nerve 235 in the patient's neck. The electrode assembly 225 preferably comprises a bipolar stimulating electrode pair 226, 228, such as the electrode pair described in U.S. Pat. No. 4,573,481 issued Mar. 4, 1986 to Bullara, which is hereby incorporated by reference herein in its entirety. Persons of skill in the art will appreciate that many electrode designs could be used in the present invention. The two electrodes 226, 228 are preferably wrapped about the vagus nerve, and the electrode assembly 225 secured to the nerve 235 by a spiral anchoring tether 230 such as that disclosed in U.S. Pat. No. 4,979,511 issued Dec. 25, 1990 to Reese S. Terry, Jr. and assigned to the same assignee as the instant application.

In one embodiment, the open helical design of the electrode assembly 225 (described in detail in the above-cited Bullara patent), which is self-sizing and flexible, minimizes mechanical trauma to the nerve and allows body fluid interchange with the nerve. The electrode assembly 225 conforms to the shape of the nerve, providing a low stimulation threshold by allowing a large stimulation contact area. Structurally, the electrode assembly 225 comprises two electrode ribbons (not shown), of a conductive material such as platinum, iridium, platinum-iridium alloys, and/or oxides of the foregoing. The electrode ribbons are individually bonded to an inside surface of an elastomeric body portion of two spiral electrodes, which may comprise two spiral loops of a three-loop helical assembly.

In one embodiment, the lead assembly 230 may comprise two distinct lead wires or a coaxial cable whose two conductive elements are respectively coupled to one of the conductive electrode ribbons. One suitable method of coupling the lead wires or cable to the electrodes comprises a spacer assembly such as that depicted in U.S. Pat. No. 5,531,778 issued Jul. 2, 1996, to Steven Maschino, et al. and assigned to the same Assignee as the instant application, although other known coupling techniques may be used. The elastomeric body portion of each loop is preferably composed of silicone rubber, and the third loop acts as the anchoring tether for the electrode assembly 225.

In one embodiment, the electrode(s) 140 (1-$n$) of IMD 100 (FIG. 1) may sense or detect any target symptom parameter in the patient's body 200. For example, an electrode 140 coupled to the patient's vagus nerve may detect a hormone level for determining a normal thyroid function. The electrode(s) 140 (1-$n$) may sense or detect a metabolic disorder condition. For example, a blood metabolic sensor or any other element capable of providing a sensing signal representative of a patient's body parameter associated with activity of the thyroid gland 110 may be deployed. A scan, an ultrasound, or a needle biopsy may be performed on the patient's body 200 to detect the condition of the thyroid gland 110.

In one embodiment, the neurostimulator 205 may be programmed to deliver an electrical biasing signal at programmed time intervals (e.g., every five minutes). In an alternative embodiment, the neurostimulator 205 may be programmed to initiate an electrical biasing signal upon detection of an event or upon another occurrence to deliver therapy. Based on this detection, a programmed therapy may be determined to the patient in response to signal(s) received from one or more sensors indicative of corresponding monitored patient parameters.

The electrode(s) 140(1-$n$), as shown in FIG. 1 may be used in some embodiments of the invention to trigger administration of the electrical stimulation therapy to the vagus nerve 235 via electrode assembly 225. Use of such sensed body signals to trigger or initiate stimulation therapy is hereinafter referred to as "active," "triggered," or "feedback" modes of administration. Other embodiments of the present invention utilize a continuous, periodic or intermittent stimulus signal. These signals may be applied to the vagus nerve (each of which constitutes a form of continual application of the signal) according to a programmed on/off duty cycle. No sensors may be used to trigger therapy delivery. This type of delivery may be referred to as a "passive," or "prophylactic" therapy mode. Both active and passive electrical biasing signals may be combined or delivered by a single neurostimulator according to the present invention.

The electrical signal generator 150 may be programmed using programming software of the type copyrighted by the assignee of the instant application with the Register of Copyrights, Library of Congress, or other suitable software based on the description herein. A programming wand (not shown) may be used to facilitate radio frequency (RF) communication between the external programming user interface 202 and the electrical signal generator 150. The wand and software permit noninvasive communication with the electrical signal generator 150 after the neurostimulator 205 is implanted. The wand may be powered by internal batteries, and provided with a "power on" light to indicate sufficient power for communication. Another indicator light may be provided to show that data transmission is occurring between the wand and the neurostimulator 205.

In one embodiment, a pain therapy may be administered by stimulation of the patient's vagus nerve by an application of the electrical signal 105 to the vagus nerve 235 to excite primarily the small afferent nerve fibers. The neurostimulator 205 may provide the hormonal therapy to a metabolic disorder where the patient is suffering from a metabolic imbalance. The neurostimulator 205 may provide vagus nerve stimulation (VNS) therapy in the patient's neck, i.e., the cervical region using a vagus nerve branch. The neurostimulator 205 may be activated manually or automatically to deliver the electrical bias signal to the selected cranial nerve via the electrode(s) 226, 228. The neurostimulator 205 may be programmed to deliver the electrical signal 105 continuously, periodically or intermittently when activated.

FIG. 3 shows a schematic front view of anatomy of the neck in the region of the thyroid gland 110 of a patient with attention to branches of the vagus nerve 235, such as a recurrent laryngeal nerve 300 and an inferior thyroid nerve 305 originating from the recurrent laryngeal nerve 300. One or more branches of the vagus nerve 235 innervate the thyroid gland 110 in the vicinity of the larynx 112a. Left and right branches of the nerves 300 and 305 pass under the arteries from the vicinity of the trachea 112b to meet at the two lobes of the thyroid gland 110.

The neurostimulator 205 may apply the electrical signal 115 to the selected cranial nerve 105, i.e., the vagus verve 235, or directly to the nerve branch 120, such as a vagus verve branch, e.g., the recurrent laryngeal nerve 300 and/or the inferior thyroid nerve 305. The electrical signal 115 may comprise a programmed signal to correct a chemical imbalance by elevating or dropping hormone levels in the blood stream of the patient's body 200 to treat a metabolic disorder. Application of action potentials based on the electrical signal 115 to the nerves 300 and/or 305 may adjust hormone levels associated with the thyroid gland 110. The electrical signal 115 may alter composite (multi-axon, multi-purpose) cranial nerve signals. The vagus nerve 235 comprises tens of thousands of individual nerve axons, each of which generally conducts an electrical signal in only one direction: either to the brain (afferent fibers) or from the brain (efferent fibers). Thus, the vagus nerve 235 comprises a composite of many individual nerve fibers transmitting information to and from the brain 125.

Stimulation from the electrical signal generator 150 may improve the hormonal performance of the thyroid gland 110. Accordingly, the IMD 100 may substantially reduce hormonal imbalance as perceived by the brain 125. By producing afferent and/or efferent action potentials for nerve fibers, the neurostimulator 205 may treat a metabolic disorder.

Figure 4A:
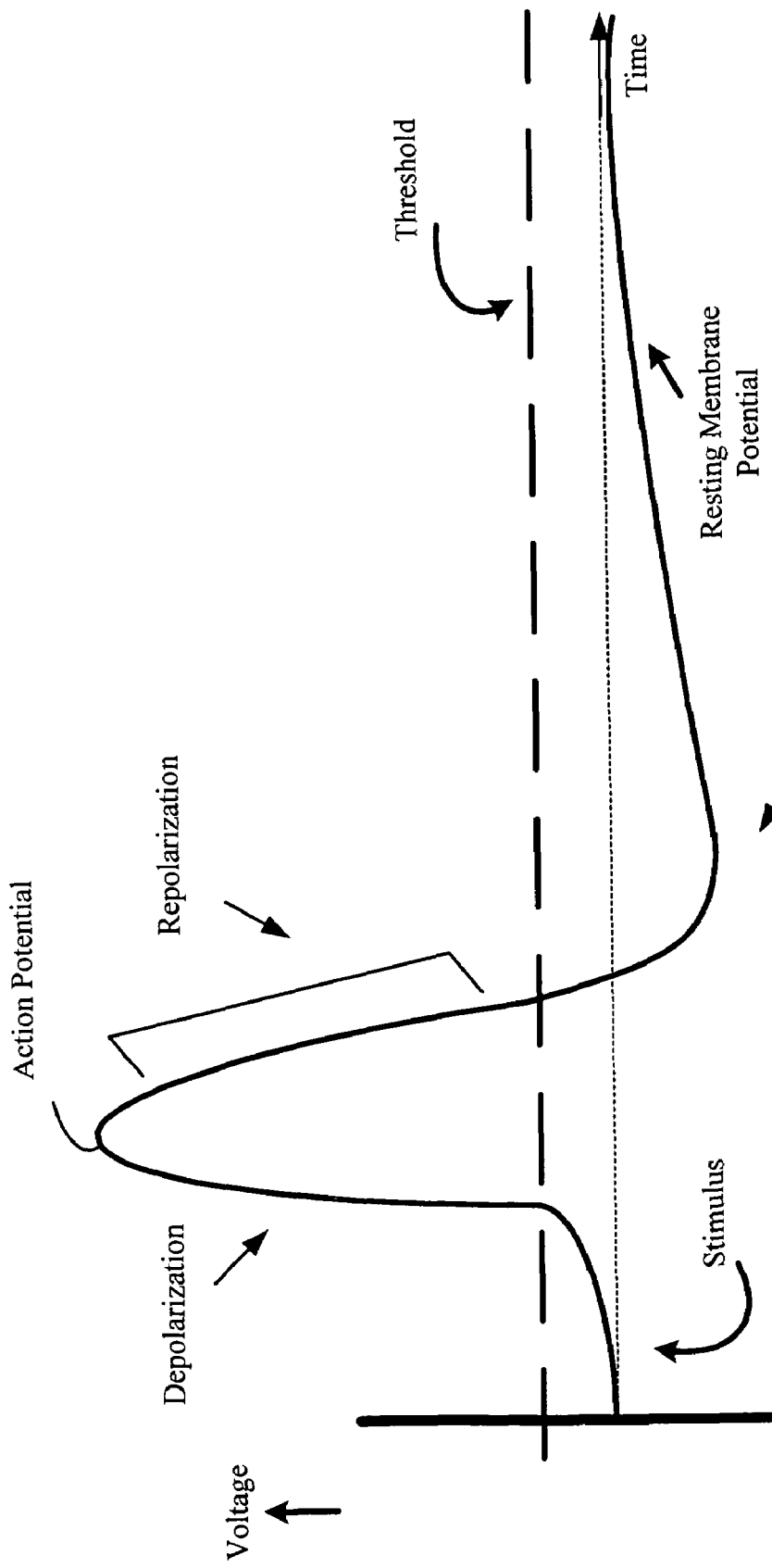
FIG. 4A illustrates an exemplary electrical signal of a firing neuron as a graph of voltage at a given location at particular times during firing by the neurostimulator of FIG. 2, when applying an electrical signal to the vagus nerve, in accordance with one illustrative embodiment of the present invention.

FIG. 4A shows an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

Figure 4B:
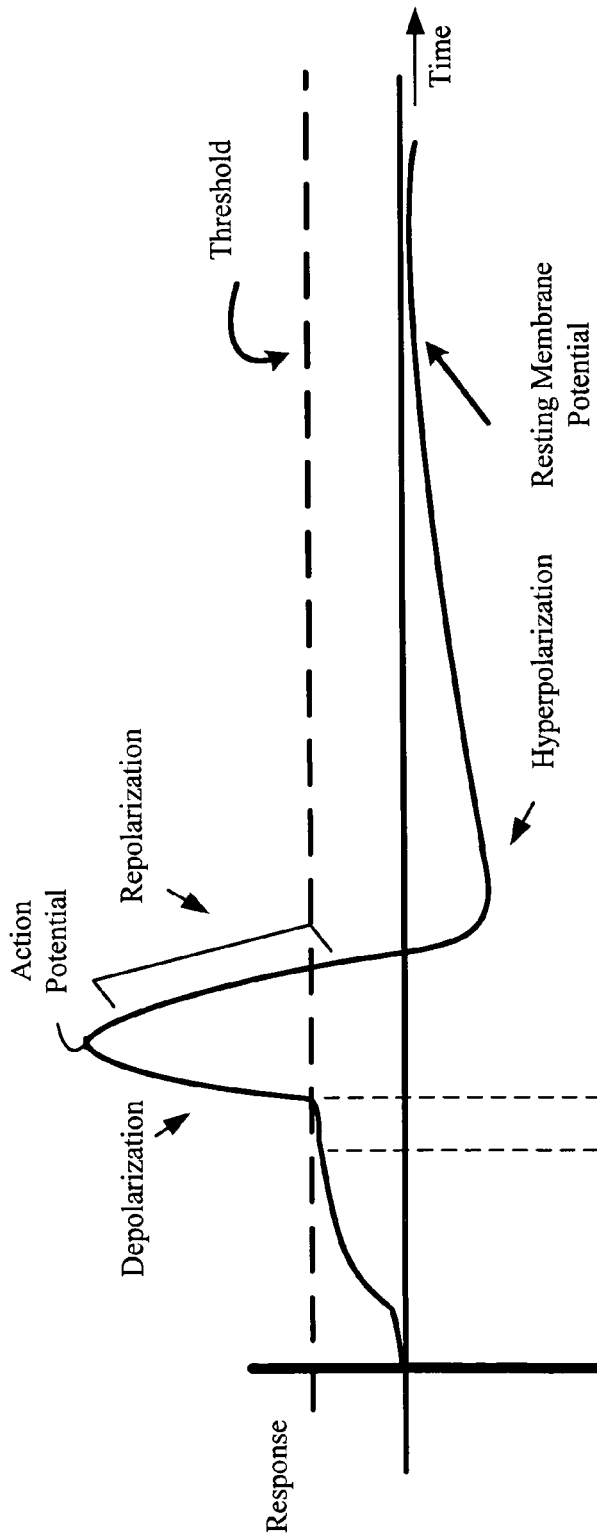
FIG. 4B illustrates an exemplary electrical signal response of a firing neuron as a graph of voltage at a given location at particular times during firing by the neurostimulator of FIG. 2, when applying a sub-threshold depolarizing pulse and additional stimulus to the vagus nerve, in accordance with one illustrative embodiment of the present invention.
Figure 4C:
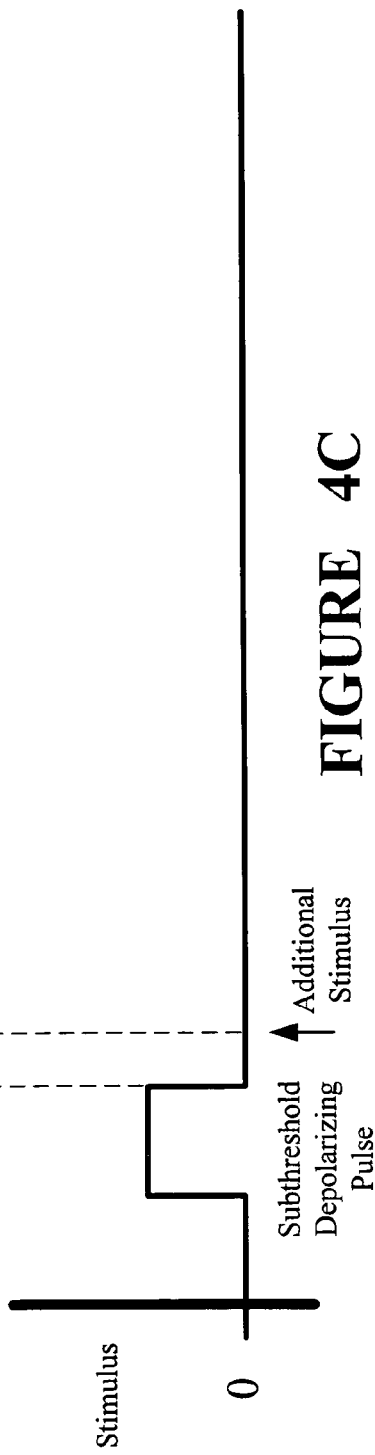
FIG. 4C illustrates an exemplary stimulus including a sub-threshold depolarizing pulse and additional stimulus to the vagus nerve for firing a neuron as a graph of voltage at a given location at particular times by the neurostimulator of FIG. 2, in accordance with one illustrative embodiment of the present invention.

Referring to FIG. 4B, an exemplary electrical signal response is illustrated of a firing neuron as a graph of voltage at a given location at particular times during firing by the neurostimulator of FIG. 2, in accordance with one illustrative embodiment of the present invention. As shown in FIG. 4C, an exemplary stimulus including a sub-threshold depolarizing pulse and additional stimulus to the cranial nerve 105, such as the vagus nerve 235 may be applied for firing a neuron, in accordance with one illustrative embodiment of the present invention. The stimulus illustrated in FIG. 4C depicts a graph of voltage at a given location at particular times by the neurostimulator of FIG. 2.

The neurostimulator may apply the stimulus voltage of FIG. 4C to the cranial nerve 105, which may include afferent fibers, efferent fibers, or both. This stimulus voltage may cause the response voltage shown in FIG. 4B. Afferent fibers transmit information to the brain from the extremities; efferent fibers transmit information from the brain to the extremities. The vagus nerve 235 may include both afferent and efferent fibers, and the neurostimulator 205 may be used to stimulate either or both. The cranial nerve 105 may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa.

Figures 5A, 5B:
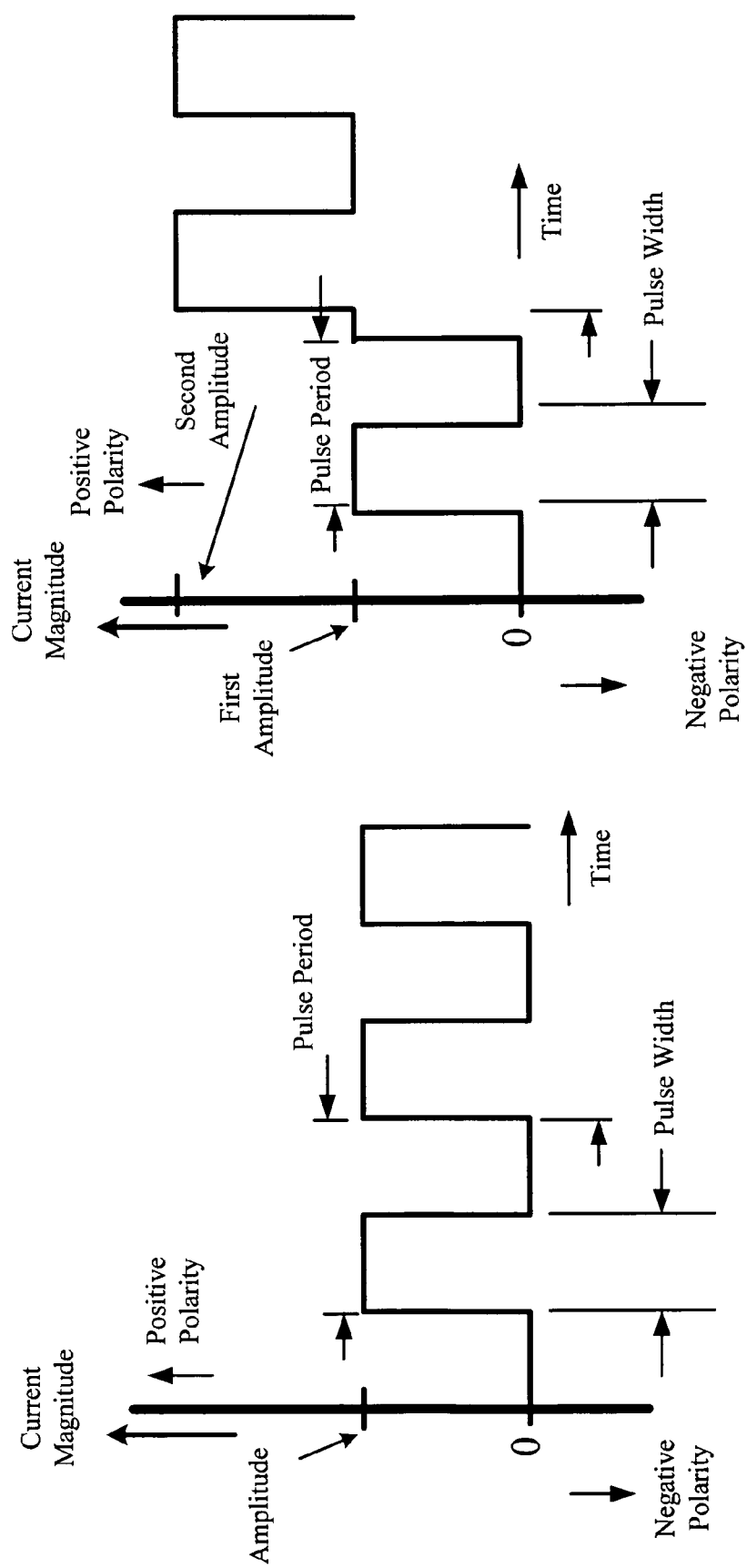
FIG. 5 illustrates exemplary waveforms for generating the electrical signals that may be based on an amount of at least one of a thyroid hormone and a thyroid-stimulating hormone in the blood of the patient relative to a value within a defined range, according to one illustrative embodiment of the present invention.
Figure 5C:
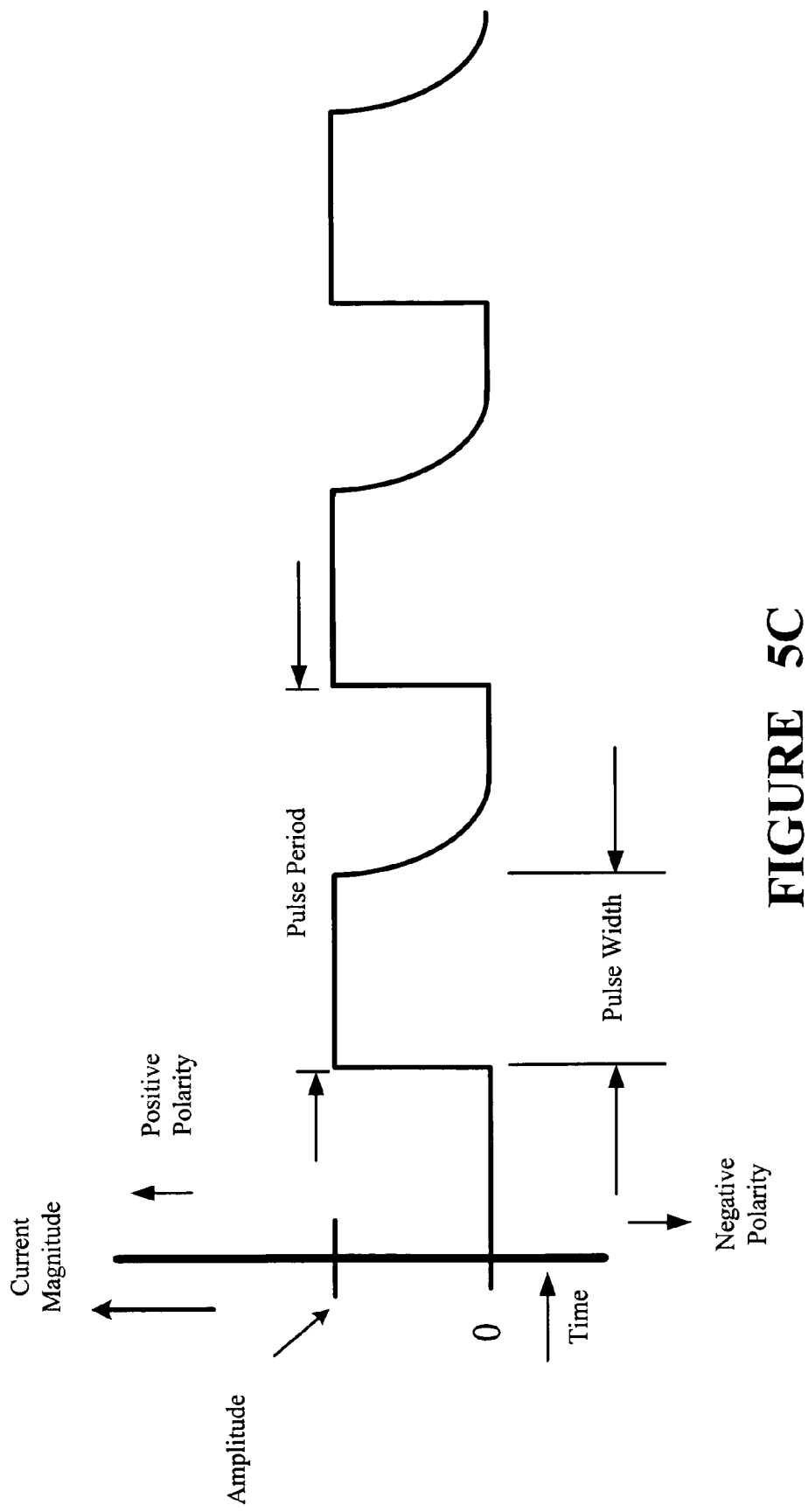

Returning to FIG. 2, the neurostimulator 205 may generate the electrical signal 115 according to one or more programmed parameters for stimulation of the vagus nerve 235. In one embodiment, the stimulation parameter may be selected from the group consisting of a current magnitude, a pulse frequency, a signal width, on-time, and off-time. An exemplary table of ranges for each of these stimulation parameters is provided in Table 1. The stimulation parameter may be of any suitable waveform; exemplary waveforms in accordance with one embodiment of the present invention are shown in FIGS. 5A to 5C. Specifically, the exemplary waveforms 5A to 5C depict generation of the electrical signal 115 that may be based on an amount of at least one of a thyroid hormone and a thyroid-stimulating hormone in the blood and/or detect a thyroid-stimulating biochemical function of the patient relative to a value within a defined range.

According to one illustrative embodiment of the present invention, various electrical signal patterns may be employed by the neurostimulator 205. These electrical signals may include a plurality of types of pulses, e.g., pulses with varying amplitudes, polarity, frequency, etc. For example, the exemplary waveform 5A depicts that the electrical signal 115 may be defined by fixed amplitude, constant polarity, pulse width, and pulse period. The exemplary waveform 5B depicts that the electrical signal 115 may be defined by a variable amplitude, constant polarity, pulse width, and pulse period. The exemplary waveform 5C depicts that the electrical signal 115 may be defined by a fixed amplitude pulse with a relatively slowly discharging current magnitude, constant polarity, pulse width, and pulse period. Other types of signals may also be used, such as sinusoidal waveforms, etc. The electrical signal may be controlled current signals.

TABLE 1

| Parameter | Range |
| --- | --- |
| Output current | 0.1-6.0 mA |
| Pulse width | 10-1500 μsec |
| Frequency | 0.5-250 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals may be generated for stimulating the nerve 105 during the on-time. Such a sequence may be referred to as a "pulse burst." This sequence may be followed by a period in which no signals are generated. During this period, the nerve is allowed to recover from the stimulation during the pulse burst. The on/off duty cycle of these alternating periods of stimulation and idle periods may have a ratio in which the off-time may be set to zero, providing continuous stimulation. Alternatively, the idle time may be as long as one day or more, in which case the stimulation is provided once per day or at even longer intervals. Typically, however, the ratio of "off-time" to "on-time" may range from about 0.5 to about 10.

In one embodiment, the width of each signal may be set to a value not greater than about 1 msec, such as about 250-500 μsec, and the signal repetition frequency may be programmed to be in a range of about 20-250 Hz. In one embodiment, a frequency of 150 Hz may be used. A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

In one embodiment, the present invention may include coupling of at least one electrode to each of two or more cranial nerves. (In this context, two or more cranial nerves means two or more nerves having different names or numerical designations, and does not refer to the left and right versions of a particular nerve). In one embodiment, at least one electrode 140 may be coupled to each of the vagus nerve 235 and/or a branch of the vagus nerve. The electrode may be operatively coupled to thyroid gland 110. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the neurostimulator 205 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the vagus nerve 235 and the additional impedance of the skin of the patient. Although external systems typically require greater power consumption than implantable ones, they have an advantage in that their batteries may be replaced without surgery.

External stimulation may be used as a screening test to determine if the patient should receive an implanted cranial nerve stimulation system. In one embodiment, the invention includes stimulating the trigeminal nerve, the glossopharyngeal nerve, and/or the vagus nerve 235 with an external skin-mounted electrode to determine if the patient is responsive to cranial nerve stimulation for treating the metabolic disorder. A lead may connect the skin electrode to an electrical pulse generator carried by the patient, e.g., in a pocket or mounted on a belt. The patient may be subjected to relatively high stimulation for a first test period to determine whether the patient's vocal cord disorder is amenable to treatment with cranial nerve stimulation. The symptoms of the patient may be analyzed following the first test period, and subsequently, a decision may be made whether or not implantation of an implantable system is desirable. If the metabolic disorder is treated, the patient may be considered for an implanted system to provide substantially direct coupling to a cranial nerve. In certain embodiments, both external stimulation and internal stimulation may be employed to treat the metabolic disorder associated with the thyroid gland 110.

Other types of indirect stimulations may be performed in conjunction with embodiments of the invention. In one embodiment, the invention includes providing noninvasive transcranial magnetic stimulation (TMS) to the brain 125 of the patient along with the IMD 100 of the present information to treat the metabolic disorder. TMS systems include those disclosed in U.S. Pat. Nos. 5,769,778; 6,132,361; and 6,425,852. Where TMS is used, it may be used in conjunction with cranial nerve stimulation as an adjunctive therapy. In one embodiment, both TMS and direct cranial nerve stimulation may be performed to treat the vocal cord disorder.

Returning to systems for providing direct cranial nerve stimulation, such as that shown in FIGS. 1 and 2, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. For example, if the patient undergoes an acute episode of the metabolic disorder, the patient may manually activate the neurostimulator 205 to stimulate the cranial nerve 105 to treat the acute episode. The patient may also be permitted to alter the intensity of the signals applied to the cranial nerve within limits established by the physician. For example, the patient may be permitted to alter the signal frequency, current, duty cycle, or a combination thereof. In at least some embodiments, the neurostimulator 205 may be programmed to generate the stimulus for a relatively long period of time in response to manual activation.

Patient activation of a neurostimulator 205 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 150 may include a sensor such as piezoelectric element mounted to the inner surface of the generator case and adapted to detect light taps by the patient on the implant site. One or more taps applied in fast sequence to the skin above the location of the electrical signal generator 150 in the patient's body 200 may be programmed into the implanted medical device 100 as a signal for activation of the electrical signal generator 150. Two taps spaced apart by a slightly longer duration of time may be programmed into the IMD 100 to indicate a desire to deactivate the electrical signal generator 150, for example. The patient may be given limited control over operation of the device to an extent which may be determined by the program dictated or entered by the attending physician. The patient may also activate the neurostimulator 205 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a temperature sensor, a blood parameter sensor, a heart parameter sensor, a brain parameter sensor, or a sensor for another body parameter. The sensor may also include a nerve sensor for sensing activity on a nerve, such as a cranial nerve, such as the vagus nerve 235.

In one embodiment, the sensor may sense a body parameter that corresponds to a symptom of metabolic disorder. If the sensor is to be used to detect a symptom of the medical disorder, a signal analysis circuit may be incorporated into the neurostimulator 205 for processing and analyzing signals from the sensor. Upon detection of the symptom of the metabolic disorder, the processed digital signal may be supplied to a microprocessor in the neurostimulator 205 to trigger application of the electrical signal 115 to the cranial nerve 105. In another embodiment, the detection of a symptom of interest may trigger a stimulation program including different stimulation parameters from a passive stimulation program. This may entail providing a higher current stimulation signal or providing a higher ratio of on-time to off-time.

The neurostimulator 205 may be implanted into the patient's body 200 for applying the electrical signal 115 to the vagus nerve 235, in accordance with one illustrative embodiment of the present invention. For example, a metabolic disorder treatment system may comprise a detection communicator, which may be a portion of the controller 155 capable of delivering at least one signal to the electrical signal generator 150. For example, the detection communicator may detect an indication of a symptom characteristic of a disorder associated with the thyroid gland 110. The electrical signal generator 150 may be capable of applying the electrical signal 115 on receipt of a signal from the detection communicator to treat a metabolic disorder. The electrical signal generator 150 may generate afferent action potentials on the vagus nerve 235 based on the symptom characteristic to improve the condition of the disorder associated with the thyroid gland 110. Examples of the metabolic disorder associated with the thyroid gland 110 may include a growth hormone secretion disorder and a vocal cord disorder.

In response to the afferent action potentials, the detection communicator may detect an indication of change in the symptom characteristic. The detection communicator may provide feedback for the indication of change in the symptom characteristic to modulate the electrical signal 115. In response to providing feedback for the indication, the electrical signal generator 150 may adjust the afferent action potentials to enhance efficacy of a drug in the patient.

The neurostimulator 205 may use the memory 165 to store disorder data and a routine to analyze this data. The disorder data may include sensed body parameters or signals indicative of the sensed parameters. The routine may comprise software and/or firmware instructions to analyze the sensed hormonal activity for determining whether electrical neurostimulation would be desirable. If the routine determines that electrical neurostimulation is desired, then the neurostimulator 205 may provide an appropriate electrical signal to a neural structure, such as the vagus nerve 235.

However, patient parameters that provide an indication of a medical condition or an indication of an event necessitating neurostimulation therapy generally vary from patient to patient. For example, action potentials on the vagus nerve 235 during a metabolic disorder may be detectable by measuring hormone fluctuations using a metabolic blood sensor. The measured hormone fluctuations may differ among patients experiencing the same type of metabolic disorder. Accordingly, the routine may modify the operation of the implanted neurostimulator 205 to a particular patient in response to the sensed disorder data.

In certain embodiments, the IMD 100 may comprise a neurostimulator 205 having a case 215 as a main body in which the electronics described in FIGS. 1-2 may be enclosed and hermetically sealed. Coupled to the main body may be the header 220 designed with terminal connectors for connecting to a proximal end of the electrically conductive lead(s) 135. The main body may comprise a titanium shell, and the header may comprise a clear acrylic or other hard, biocompatible polymer such as polycarbonate, or any material that may be implantable into a human body. The lead(s) 135 projecting from the electrically conductive lead assembly 230 of the header may be coupled at a distal end to electrodes **140(1-*n*). The electrodes 140(1-*n*) may be coupled to neural structure such as the vagus nerve 235, utilizing a variety of methods for operatively coupling the lead(s) 135 to the tissue of the vagus nerve 235. Therefore, the current flow may take place from one terminal of the lead 135 to an electrode such as electrode 226 (FIG. 2) through the tissue proximal to the vagus nerve 235, to a second electrode such as electrode 228 and a second terminal of the lead 135**.

Figure 6:
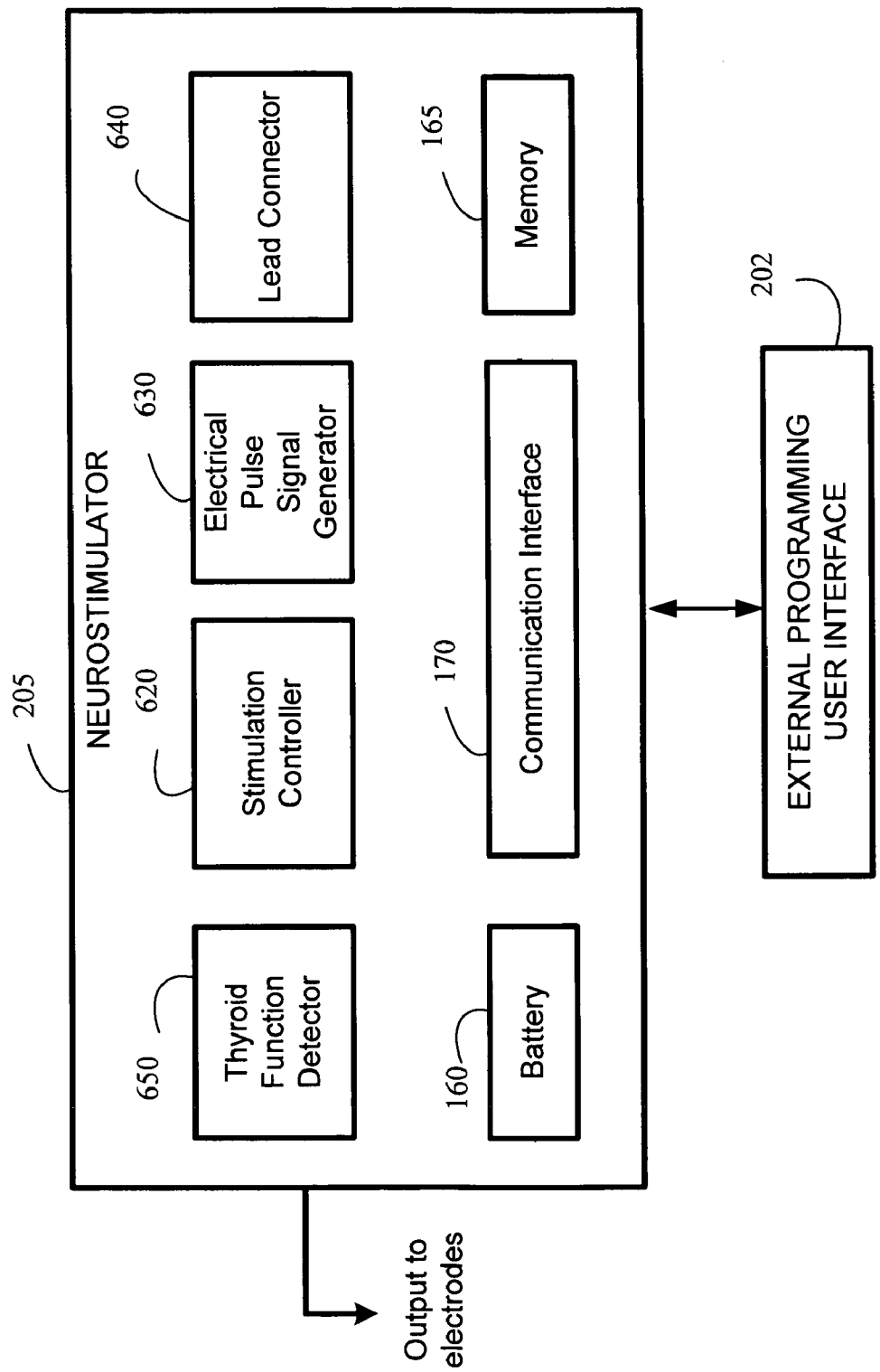
FIG. 6 is a stylized schematic representation of an implantable medical device that includes a detection communicator, in accordance with one illustrative embodiment of the present invention.

Turning now to FIG. 6, a stylized schematic representation of an IMD 100, such as the neurostimulator 205 is depicted to include a thyroid function detector 650, in accordance with one illustrative embodiment of the present invention. The neurostimulator 205 includes the battery 160 capable of providing power to operate, a stimulation controller 620 to authorize generation of an electrical stimulation signal. The neurostimulator 205 also includes an electrical pulse signal generator 630 to generate an electrical pulse stimulus upon authorization by the stimulation controller 620 and to provide the electrical pulse stimulus to a lead connector 640. The battery 160 is also capable of providing power to the thyroid function detector 650. The thyroid function detector 650 is capable of delivering at least one control signal to the stimulation controller 620. Upon receipt of a control signal from the thyroid function detector 650 of authorizing an electrical pulse stimulus, the stimulation controller 620 prompts the electrical pulse signal generator 630 to provide a stimulation signal.

The thyroid function detector 650 may detect or sense a function or dysfunction of the thyroid gland 110. For example, the thyroid function detector 650 may detect or sense release of thyroid stimulating hormone (TSH) in response to thyrotropin releasing hormone (TRH) in the presence of normal or raised concentrations of circulating TSH and normal concentrations of clinical thyroxine ($T_4$) and tri-iodothyronine ($T_3$). The thyroid function detector 650 may use any one of or a combination of a variety of detection and sensing techniques including endocrinological and biochemical techniques to detect or sense a function or dysfunction of the thyroid gland 110. Thyroid dysfunction is a common disorder in patients suffering from a chronic or recurrent affective illness that is treatment-resistant, hypothalamic-pituitarythyroid axis function. For example, sub-clinical forms of hypothyroidism may occur in bipolar patients treated with lithium and in a subgroup of rapid cycling manic-depressive patients.

The thyroid function detector 650 may perform a thyroid function test based on measurements of thyroid-simulating hormone (TSH), serum triiodothyronine ($T_3$) uptake, total serum thyroxine assay ($T_4$), free $T_4$, and serum antithyroid globulin titers. The testing of TSH may enable assessing of the thyroid function. Baseline thyroid function may be obtained prior to or at the start of lithium therapy in some patients. The thyroid function detector 650 may determine whether the TSH has become elevated, indicating a need for thyroid replacement therapy. The thyroid function detector 650 may indicate a normal serum thyroid stimulating hormone (TSH) concentration to exclude hypothyroidism or hyperthyroidism.

The thyroid function detector 650 may ascertain a thyrotoxicosis condition characterized by biochemical and psychological changes resulting from a chronic excess of endogenous thyroid hormone. The thyrotoxicosis condition may be detected based on increased $T_3$, $T_4$, and free thyroxine index and increased radioactive iodine uptake. Serum $T_3$ is usually increased more than serum $T_4$. Manifestations of thyrotoxicosis may include tachycardia; gastrointestinal disturbances; hyperthermia; panic, anxiety, and agitation; and mania, dementia, and psychosis. Other symptoms include tremor, sweating, weight loss, and heat intolerance.

The thyroid function detector 650 may detect thyrotropin (TSH) (Thytropar) hormone, secreted by the adenohypophysis of the pituitary gland, which regulates formation and secretion of thyroid hormone to test ability of the thyroid gland 110 to respond to exogenous stimulation. The thyroid function detector 650 may detect thyrotropin releasing factor (TRF), one of the hypothalamic hypophysiotropic factors, which exert biological actions on the central nervous system.

The thyroid function detector 650 may detect thyrotropin releasing hormone (TRH). Endogenous tripeptide found heterogenously throughout the central nervous system and causes release of prolactin to regulate thyroid-stimulating hormone (TSH). The thyroid-stimulating hormone stimulates release of triiodothyronine ($T_3$) and thyroxine ($T_4$) hormone secretion from the thyroid gland 110. The thyroid stimulating hormone functions as a neuromodulator for a variety of neurotransmitters, including serotonin and dopamine. The thyrotropin releasing hormone may relieve tension and anxiety in humans. In normal men, intravenous TRH administration produces maximal secretion of thyrotropin within 15-30 minutes. When administered to depressed patients, some patients may exhibit blunted TSH response and others may exhibit an exaggerated response. A rapid, transient improvement in mood and other depressive symptoms in depressed patients may be obtained based on a TRH test administration on depression assessments.

A TSH response to TRH may be detected by the thyroid function detector 650 and a TSH response may indicate major depression in some patients. The TRH test may assess hypothalamic-pituitary dysregulation in depressive states. The thyroid function detector 650 may perform a thyrotropin releasing hormone (TRH) stimulation test (TRH-ST) in which secretion of thyroid-stimulating hormone (TSH) may be measured following a TRH infusion. The TRH-ST test may provide a measure of hypothalamic-pituitary-thyroid (HPT) axis function because it is affected both by feedback regulation from the thyroid and feed-forward regulation from the hypothalamic release and release-inhibiting hormones TRH and somatostatin. A blunted TSH response to TRH may indicate a depressed patient. Some depressed patients may exhibit exaggerated TSH response to TRH. Such depressed patients with exaggerated TSH responses to TRH and normal baseline TSH and thyroid hormone concentrations have, by definition, grade 3 hypothyroidism.

The thyroid function detector 650 may test levels for the thyroxine ($T_4$; tetraiodothyronine) (Eltioxin; Euthroid; Levothroid Synthroid), a naturally occurring hormone produced by the thyroid gland 110. The $T_4$ level is low in patients with hypothyroidism. The thyroxine test may be used in treatment of congenital or acquired hypothyroidism, suppression of goiter, and to treat thyrotoxicosis in conjunction with antithyroid drugs. Dosages ranging from 100 to 200 1 1 g/day are usually sufficient to maintain a euthyroid state in patients treated for hypothyroidism, resulting in increased physical and mental well-being, weight reduction, and improved tolerance of cold, relief of constipation, increased heart rate, and peripheral vascular perfusion. The $T_4$ hormone as used often by psychiatrists as an adjunct to antidepressants may enhance therapeutic response and convert a partial responder or treatment-resistant patient into a therapeutic responder. For example, high doses may prevent rapid cycling in treatment-resistant bipolar patients.

The thyroid function detector 650 may test for levels of the thyroxine binding globulin (TBG). Acidic glycoprotein, a major carrier of thyroid hormones, provides protein binding of thyroid hormones and protects them from metabolism and excretion, resulting in their long half-life in the circulation. High doses of thyroxine combined with lithium may decrease cycling frequency and severity in rapid cycling bipolar disorder.

In one embodiment, the stimulation controller 620 defines the electrical stimulus pulses to be delivered to the nerve tissue according to parameters based on the results from one or more tests of thyroid function and may be preprogrammed into the neurostimulator 205. The stimulation controller 620, which may include a processor that may execute program code, controls the operation of the electrical pulse signal generator 630. The electrical pulse signal generator 630 is capable of generating the stimulus pulses according to programmed parameters and providing these pulses to the lead connector 640 for delivery to the patient. The stimulation controller 620 may be capable of implementing multi-phasic controlled current signal outputs. The stimulation controller 620 may be capable of providing a controlled current signal where pulses may include various amplitudes, varying phases, and varying polarity. The stimulation controller 620 may also be capable of providing mono-phasic stimulation signals. The stimulation controller 620 may also be capable of switching between various electrodes employed by the neurostimulator 205.

In an alternative embodiment, based upon various parameters provided to the neurostimulator 205, the stimulation controller 620 may develop a multi-phasic pulse description pattern and provide the description pattern to the electrical signal generator 630 to perform a particular type of multi-phasic stimulation. The stimulation controller 620 may be capable of converting stored data relating to the phasic pulse description and may control behavior of the electrical pulse signal generator 630 accordingly. Additionally, the neurostimulator 205 may also include a burst description array that includes data relating to performing a pulse-to-pulse variation of a stimulation signal. The stimulation controller 620 may be capable of using data from the burst description array to provide a stimulation signal that includes a pulse train, where one pulse in the pulse train may vary from another pulse in the pulse train. This pulse-to-pulse variation may include variations in the pulse width, amplitude, pulse-shape, polarity, etc.

Figure 7:
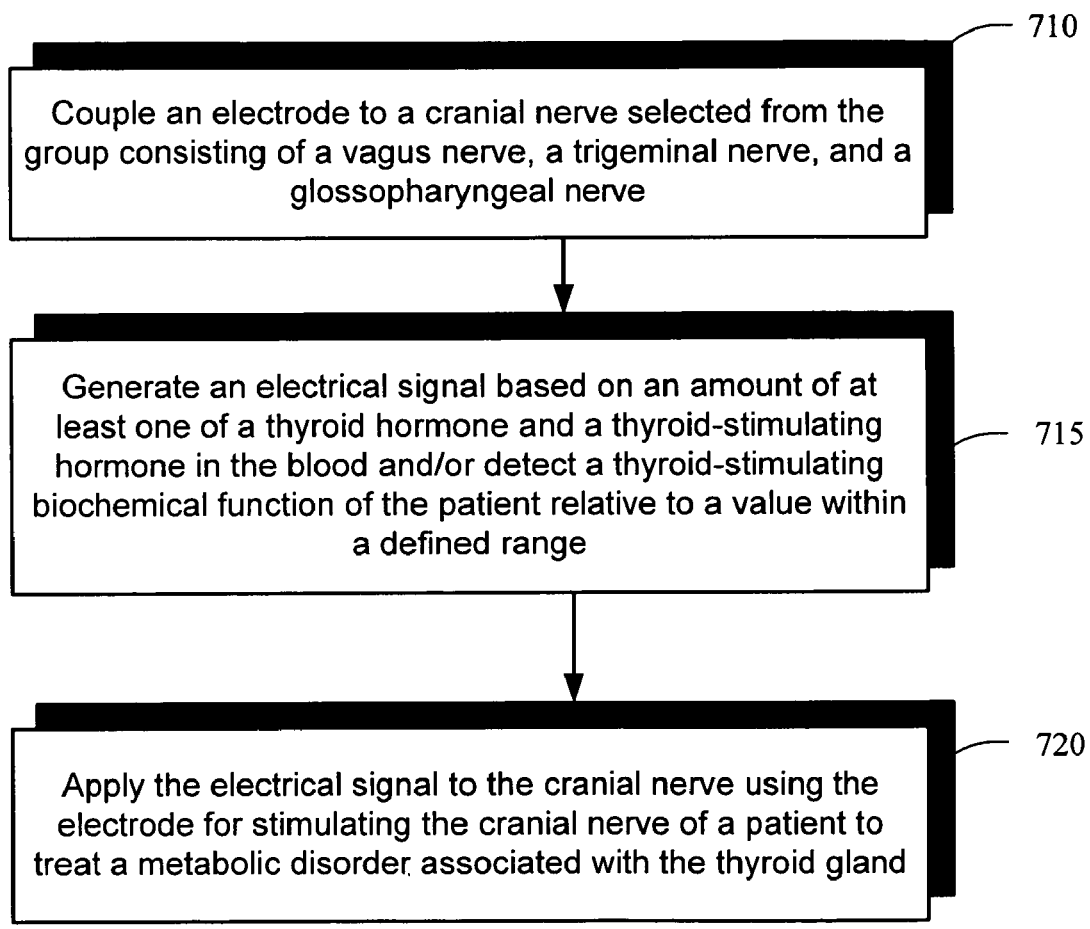
FIG. 7 is a flowchart representation of a method for stimulating a cranial nerve of a patient to treat a metabolic disorder associated with the thyroid gland using neurostimulation from an implantable medical device, in accordance with one illustrative embodiment of the present invention.

Referring to FIG. 7, a flowchart representation of a method is provided for stimulating the cranial nerve 105 of a patient to treat a metabolic disorder associated with the thyroid gland 110 using an IMD 100, in accordance with one illustrative embodiment of the present invention. The method of FIG. 7 includes (block 710) coupling at least one electrode 140 to a selected cranial nerve 105 of a patient. The method further includes generating the electrical signal 115 based upon an amount of at least one of a thyroid hormone and a thyroid-stimulating hormone in the blood and/or detect a thyroid-stimulating biochemical function of the patient relative to a value within a defined range (block 715). The IMD 100 may apply the electrical signal 115 to the cranial nerve 105 using the electrode 140 to treat a metabolic disorder associated with the thyroid gland 110. The coupling step of block 710, the generating step of block 715, and the applying step of block 720 may be performed using techniques and apparatus as described above.

Figure 8:
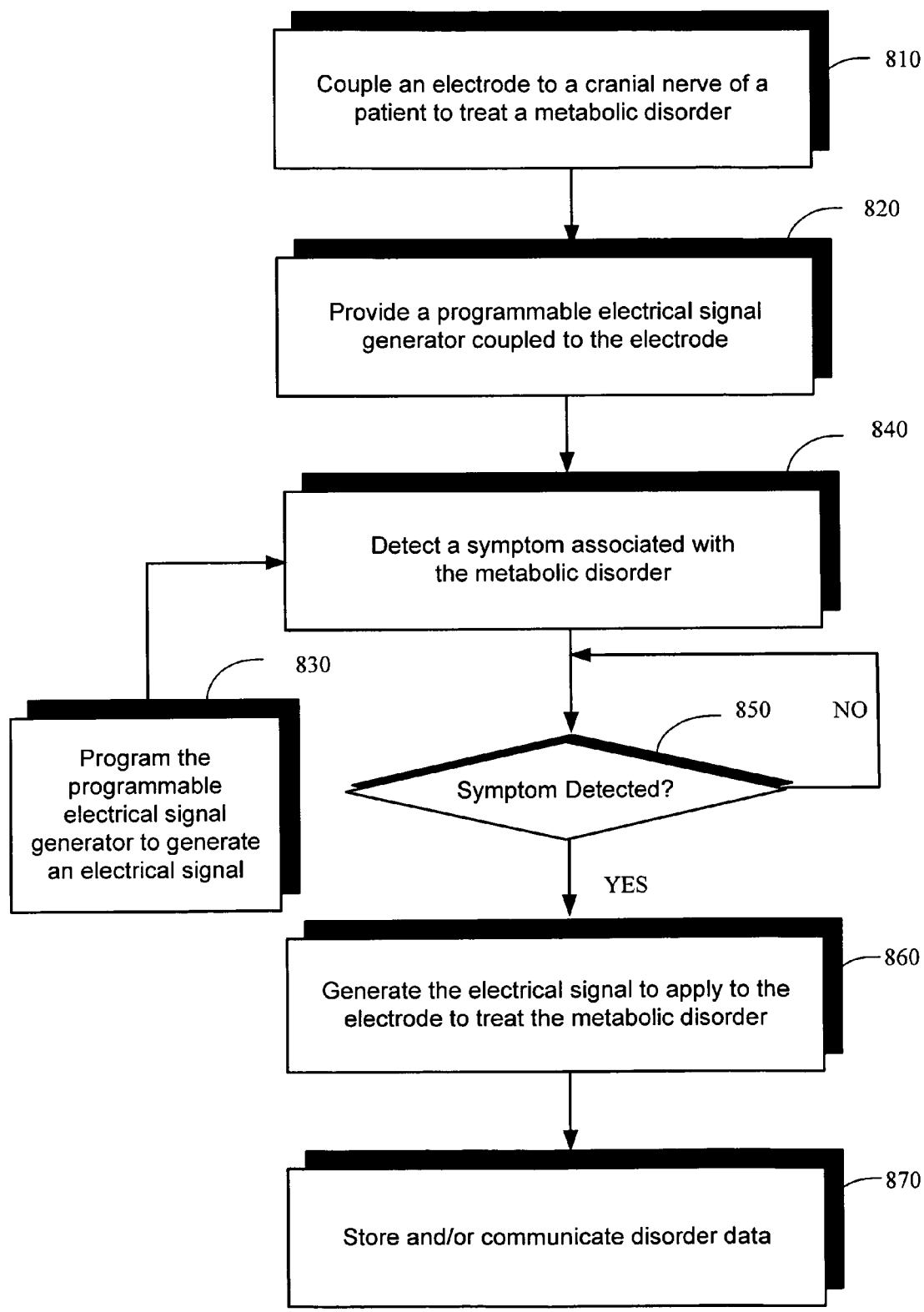
FIG. 8 is a flowchart representation of a method of treating a patient having a metabolic disorder, in accordance with one illustrative embodiment of the present invention.

Referring to FIG. 8, a flowchart representation of a method is provided for treating a patient having a metabolic disorder, in accordance with one illustrative embodiment of the present invention. The method of FIG. 8 includes coupling at least one electrode 140 to at least one cranial nerve 105 of a patient (block 810). The IMD 100 may then provide the electrical signal generator 150 coupled to the electrode 140 (block 820). The electrical signal generator 150 may be programmed in a programming step (block 830). After the electrode 140 has been coupled (block 810) and the electrical signal generator 150 has been provided (block 820), the IMD 100 may detect an event indicative of a symptom of a disorder that may be treated. In one execution of the detecting step 840, if an event is not detected, the flow of the method of FIG. 8 returns (block 860) to determine if a symptom has been detected (block 850). Alternatively, the IMD 100 may modulate an electrical stimulation signal applied to the electrode 140. If an event is detected during execution, the IMD 100 may generate an electrical stimulation signal to apply to the electrode 140 to treat the metabolic disorder. Alternatively, the IMD 100 may determine the treatment period to implement, if more than one is intended by a healthcare practitioner.

A number "n" of treatment periods designated prime, double prime ..., n-prime may be determined. Each treatment period includes generating a signal and applying the signal to the electrode coupled to the cranial nerve 105. After treatment, the results of the treatment may be stored or communicated (block 870). However, the method of FIG. 8 may be performed without a detecting step (block 840) or detection execution step (block 850). In other words, the nerve stimulation process may be performed continuously, may be performed according to a preprogrammed schedule, or may be performed after receiving input from the patient, among others.

All of the methods and apparatus disclosed and claimed herein may be made and executed without undue experimentation in light of the present disclosure. While the methods and apparatus of this invention have been described in terms of particular embodiments, it will be apparent to those of skill in the art that variations may be applied to the methods and apparatus and in the steps or in the sequence of steps of the method described herein without departing from the concept, spirit and scope of the invention as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for stimulating a cranial nerve of a patient comprising:
   coupling at least one electrode to said cranial nerve selected from the group consisting of a vagus nerve, a trigeminal nerve, and a glossopharyngeal nerve;
   generating an electrical signal to treat a disorder associated with the thyroid gland; and
   applying said electrical signal to said cranial nerve using said electrode,
   wherein said generating an electrical signal further comprises generating said electrical signal based upon an amount of at least one of a thyroid hormone, a thyroid-stimulating hormone in the blood and a thyroid-stimulating biochemical function, wherein said disorder is at least one of a metabolic and an endocrine disorder.

2. A method for stimulating a cranial nerve of a patient comprising:
   coupling at least one electrode to said cranial nerve selected from the group consisting of a vagus nerve, a trigeminal nerve, and a glossopharyngeal nerve;
   generating an electrical signal to treat a disorder associated with the thyroid gland; and
   applying said electrical signal to said cranial nerve using said electrode,
   wherein said applying said electrical signal comprises generating a response selected from the group consisting of an afferent action potential, an efferent action potential, an afferent hyperpolarization, a sub threshold depolarization and an efferent hyperpolarization, and
   wherein said applying said electrical signal comprises generating an afferent action potential for treating said disorder associated with the thyroid gland of said patient.

3. A method for stimulating a cranial nerve of a patient comprising:
   coupling at least one electrode to said cranial nerve selected from the group consisting of a vagus nerve, a trigeminal nerve, and a glossopharyngeal nerve;

generating an electrical signal to treat a disorder associated with the thyroid gland; and applying said electrical signal to said cranial nerve using said electrode, further comprising detecting a symptom of said disorder, wherein said applying said electrical signal is initiated in response to said detecting, wherein said detecting said symptom comprises using a thyroid function detector.

4. The method of claim 3, wherein said applying said electrical signal is performed during a first treatment period, and further comprises:

applying a second electrical signal to said cranial nerve using said electrode during a second treatment period to treat said disorder;

detecting a symptom of said disorder; and sensing a metabolic imbalance and said second treatment period being initiated upon said detecting said symptom.

5. A method of treating a patient having at least one of a metabolic and an endocrine disorder, comprising:

coupling at least one electrode to at least one cranial nerve of said patient, wherein said cranial nerve is selected from the group consisting of a vagus nerve, a trigeminal nerve, and a glossopharyngeal nerve;

providing a programmable electrical signal generator coupled to said electrode;

programming said programmable electrical signal generator to generate an electrical signal;

detecting a symptom associated with said at least one of a metabolic and an endocrine disorder; and in response to detecting said symptom, generating said electrical signal to apply to said electrode to treat said at least one of a metabolic and an endocrine disorder, wherein said programming said programmable electrical signal generator to generate an electrical signal further comprises generating said electrical signal based upon an amount of at least one of a thyroid hormone, a thyroid-stimulating hormone in the blood and a thyroid-stimulating biochemical function of the patient to treat said at least one of a metabolic and an endocrine disorder.

6. A method for stimulating a nerve branch associated with the thyroid gland of a patient comprising:

coupling at least one electrode to said nerve branch selected from the group consisting of a recurrent laryngeal nerve, an inferior thyroid nerve originating from the recurrent laryngeal nerve and an autonomic nerve of the autonomic nervous system; and generating an electrical signal to treat a disorder associated with the thyroid gland; and applying said electrical signal to said nerve branch using said electrode.

7. The method of claim 6, wherein said generating an electrical signal further comprises generating said electrical signal based upon an amount of at least one of a thyroid hormone, a thyroid-stimulating hormone in the blood and a thyroid-stimulating biochemical function, wherein said disorder is at least one of a metabolic and an endocrine disorder.

8. The method of claim 6, wherein said coupling said at least one electrode comprises using said electrode to stimulate said nerve branch nerve using a location selected from the group consisting of the left vagus nerve and the right vagus nerve.

9. The method of claim 6, wherein said coupling said at least one electrode comprises operatively coupling said electrode to said nerve branch using an attachment selected from the group consisting of a mechanical attachment and an electrical attachment located in proximity to said nerve branch.

10. The method of claim 6, wherein said applying said electrical signal comprises generating a response selected from the group consisting of an afferent action potential, an efferent action potential, an afferent hyperpolarization, a sub threshold depolarization and an efferent hyperpolarization.

11. The method of claim 6, wherein said applying said electrical signal comprises generating said electrical signal based on an amount of at least one of a thyroid hormone and a thyroid-stimulating hormone in the blood of the patient relative to a value within a defined range and a thyroid-stimulating biochemical function, wherein said disorder is at least one of a metabolic and an endocrine disorder.

12. A method for stimulating a vagus nerve branch associated with the thyroid gland of a patient comprising:

coupling at least one electrode to said vagus nerve branch selected from the group consisting of a recurrent laryngeal nerve and an inferior thyroid nerve originating from the recurrent laryngeal nerve; and generating an electrical signal to treat a disorder associated with the thyroid gland; and applying said electrical signal to said vagus nerve branch using said electrode.

13. The method of claim 12, wherein said generating an electrical signal further comprises generating said electrical signal based upon an amount of at least one of a thyroid hormone, a thyroid-stimulating hormone in the blood and a thyroid-stimulating biochemical function, wherein said disorder is at least one of a metabolic and an endocrine disorder.

14. The method of claim 12, wherein said coupling said at least one electrode comprises using said electrode to stimulate said vagus nerve branch using a location selected from the group consisting of the left vagus nerve and the right vagus nerve.

15. The method of claim 12, wherein said coupling said at least one electrode comprises operatively coupling said electrode to said vagus nerve branch using an attachment selected from the group consisting of a mechanical attachment and an electrical attachment located in proximity to said vagus nerve branch.

16. The method of claim 12, wherein said applying said electrical signal comprises generating a response selected from the group consisting of an afferent action potential, an efferent action potential, an afferent hyperpolarization, a sub-threshold depolarization and an efferent hyperpolarization.

17. The method of claim 12, wherein said applying said electrical signal comprises generating said electrical signal based on an amount of at least one of a thyroid hormone and a thyroid-stimulating hormone in the blood of the patient relative to a value within a defined range and a thyroid-stimulating biochemical function, wherein said disorder is at least one of a metabolic and an endocrine disorder.

* * * * *